US011331117B2

(12) United States Patent
Bleck et al.

(10) Patent No.: US 11,331,117 B2
(45) Date of Patent: May 17, 2022

(54) TISSUE EXTRACTION DEVICES AND RELATED METHODS

(71) Applicant: Freyja Healthcare, LLC, North Andover, MA (US)

(72) Inventors: James Bleck, North Andover, MA (US); John Aho, North Andover, MA (US); Thomas Eagan, North Andover, MA (US); Jonathan Towle, North Andover, MA (US); Mark Hoffman, North Andover, MA (US)

(73) Assignee: Freyja Healthcare LLC, North Andover, MA (US)

( * ) Notice: Subject to any disclaimer, the term of this patent is extended or adjusted under 35 U.S.C. 154(b) by 0 days.

(21) Appl. No.: 17/225,219

(22) Filed: Apr. 8, 2021

(65) Prior Publication Data

US 2021/0322049 A1 Oct. 21, 2021

Related U.S. Application Data

(63) Continuation of application No. PCT/US2021/021444, filed on Mar. 9, 2021.

(60) Provisional application No. 62/987,345, filed on Mar. 9, 2020, provisional application No. 63/138,441, filed on Jan. 16, 2021.

(51) Int. Cl.
*A61B 17/3205* (2006.01)
*A61B 17/02* (2006.01)
*A61B 17/32* (2006.01)

(52) U.S. Cl.
CPC ...... *A61B 17/3205* (2013.01); *A61B 17/0218* (2013.01); *A61B 17/0293* (2013.01); *A61B 2017/320052* (2013.01); *A61B 2017/320064* (2013.01)

(58) Field of Classification Search
CPC ............ A61B 17/3205; A61B 17/0218; A61B 17/0293; A61B 2017/320052; A61B 2017/320064
USPC ..................................................... 606/79–85
See application file for complete search history.

(56) References Cited

U.S. PATENT DOCUMENTS

| 4,368,734 A | 1/1983 | Banko |
| 5,336,237 A | 8/1994 | Chin et al. |
| 5,354,303 A | 10/1994 | Spaeth et al. |

(Continued)

FOREIGN PATENT DOCUMENTS

| EP | 0578997 A1 | 1/1994 |
| WO | 9709922 A1 | 3/1997 |

(Continued)

OTHER PUBLICATIONS

International Search Report and Written Opinion dated Jun. 23, 2014 for corresponding PCT Application PCT/US2014/020649 (17 pages).

(Continued)

*Primary Examiner* — Si Ming Ku
(74) *Attorney, Agent, or Firm* — Winthrop & Weinstine, P.A.

(57) ABSTRACT

In accordance with an aspect of the present disclosure, a tissue extraction device may include a bag having an interior and a plurality of cutters elements extending along an interior surface of the bag. The cutters can be offset to facilitate collapsing of the bag prior to introducing the bag into a patient.

14 Claims, 47 Drawing Sheets

(56) References Cited

U.S. PATENT DOCUMENTS

| | | |
|---|---|---|
| 5,569,284 A | 10/1996 | Young et al. |
| 5,611,803 A | 3/1997 | Heaven et al. |
| 5,735,289 A | 4/1998 | Pfeffer et al. |
| 5,836,953 A | 11/1998 | Yoon |
| 6,451,036 B1 | 9/2002 | Heitzmann et al. |
| 6,537,273 B1 | 3/2003 | Sosiak et al. |
| 9,522,034 B2 | 12/2016 | Johnson et al. |
| 9,629,618 B2 | 4/2017 | Davis et al. |
| 9,707,012 B2 | 7/2017 | Adams et al. |
| 2004/0002683 A1 | 1/2004 | Nicholson et al. |
| 2005/0267492 A1 | 12/2005 | Poncet et al. |
| 2008/0221604 A1 | 9/2008 | Kondoh et al. |
| 2009/0326546 A1 | 12/2009 | Mohamed et al. |
| 2011/0040314 A1 | 2/2011 | McGuckin, Jr. et al. |
| 2011/0046637 A1 | 2/2011 | Patel et al. |
| 2012/0203241 A1 | 8/2012 | Williamson, IV |
| 2016/0030073 A1 | 2/2016 | Isakov et al. |
| 2016/0100857 A1 | 4/2016 | Wachli et al. |
| 2016/0346000 A1 | 12/2016 | Abreu |
| 2018/0360481 A1* | 12/2018 | Bonadio ........ A61B 17/320758 |

FOREIGN PATENT DOCUMENTS

| | | |
|---|---|---|
| WO | 2014158880 A1 | 10/2014 |
| WO | 2015164591 A1 | 10/2015 |
| WO | 2017083694 A1 | 5/2017 |
| WO | 2018119473 A1 | 6/2018 |

OTHER PUBLICATIONS

International Search Report and Written Opinion dated Jan. 24, 2017 for corresponding PCT Application PCT/US2016/061595 (4 pages).

International Search Report and Written Opinion dated Apr. 19, 2018 for corresponding PCT Application PCT/US2017/068365 (9 pages).

International Search Report and Written Opinion of International Searching Authority for International Application No. PCT/US2021/021444.

Specification and Claims as filed of International Application No. PCT/US2021/021444.

* cited by examiner

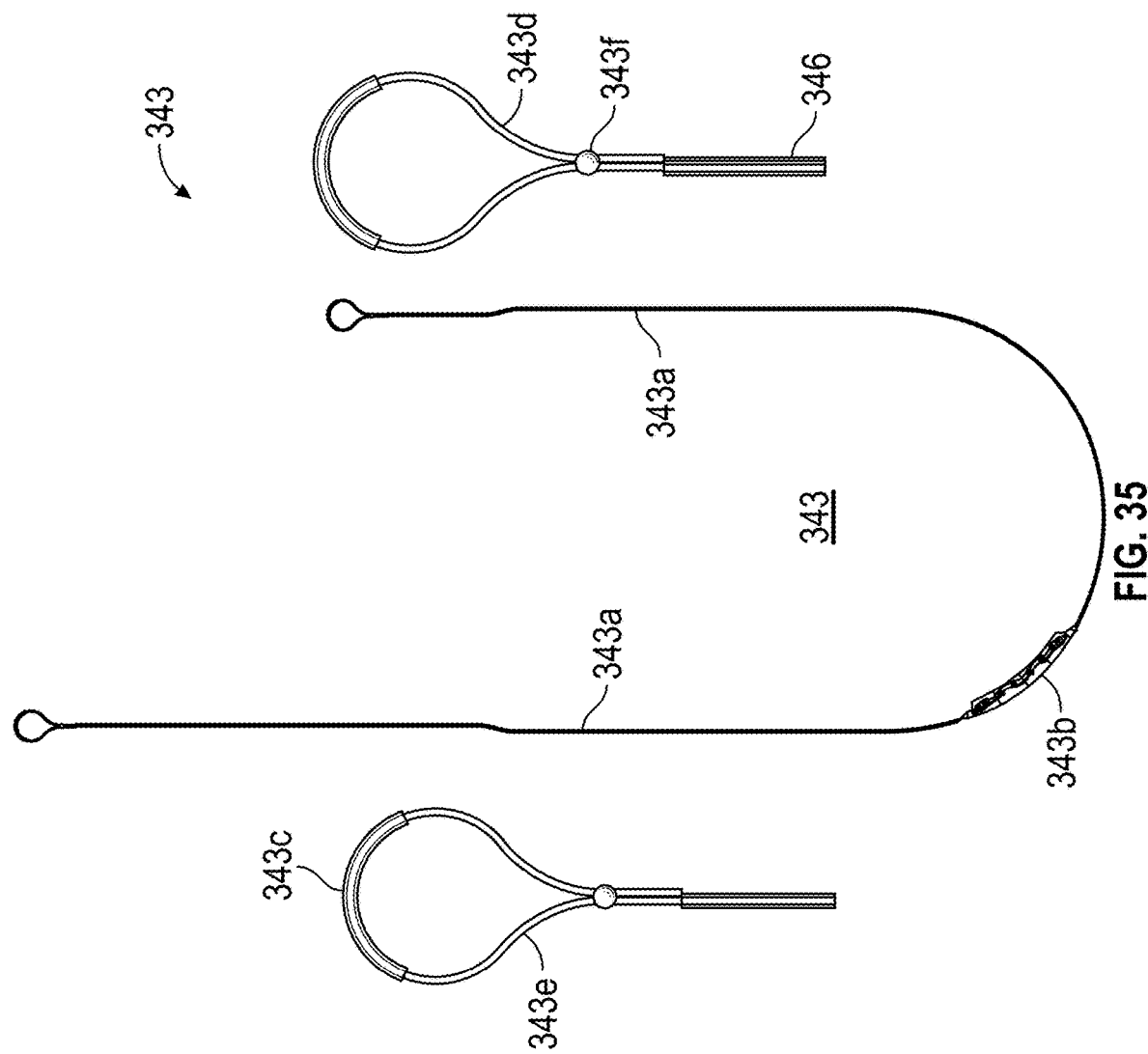

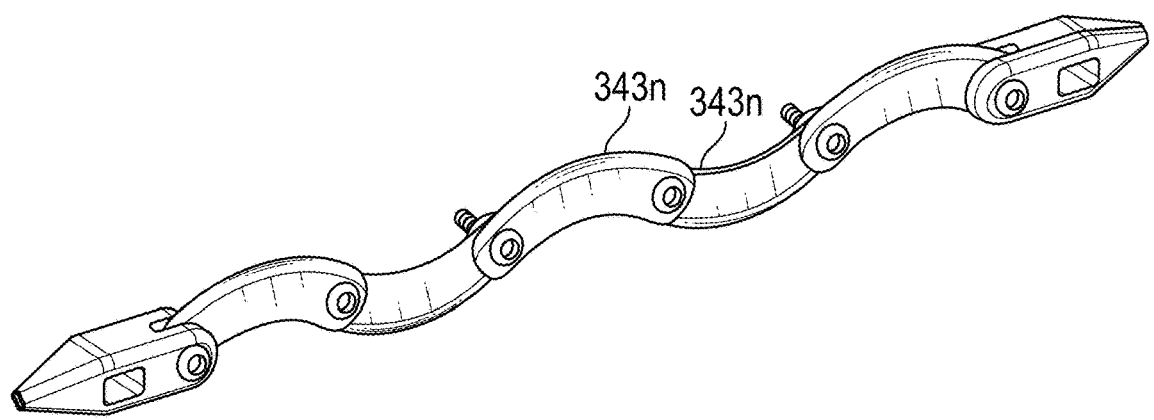
FIG. 37A
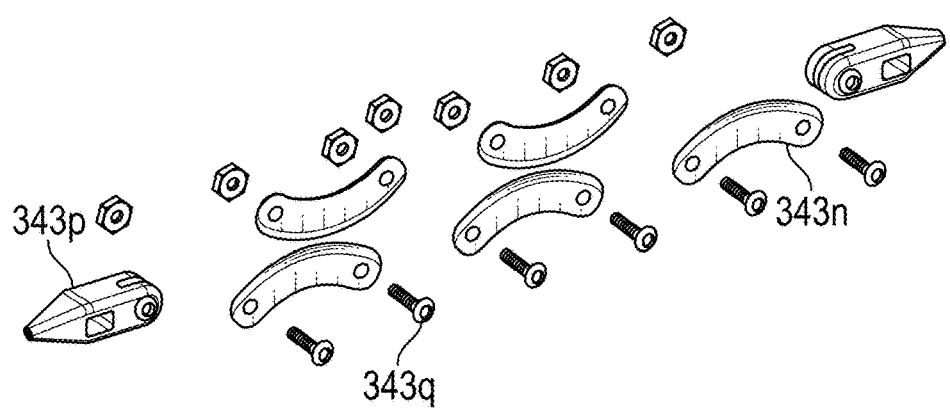
FIG. 37B
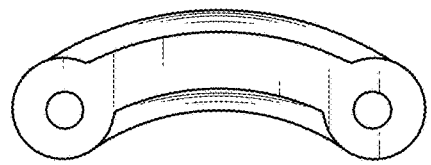
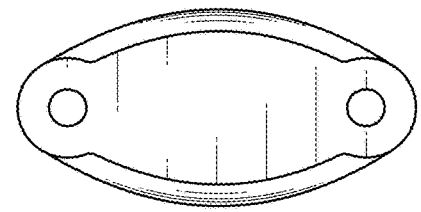
FIG. 37C

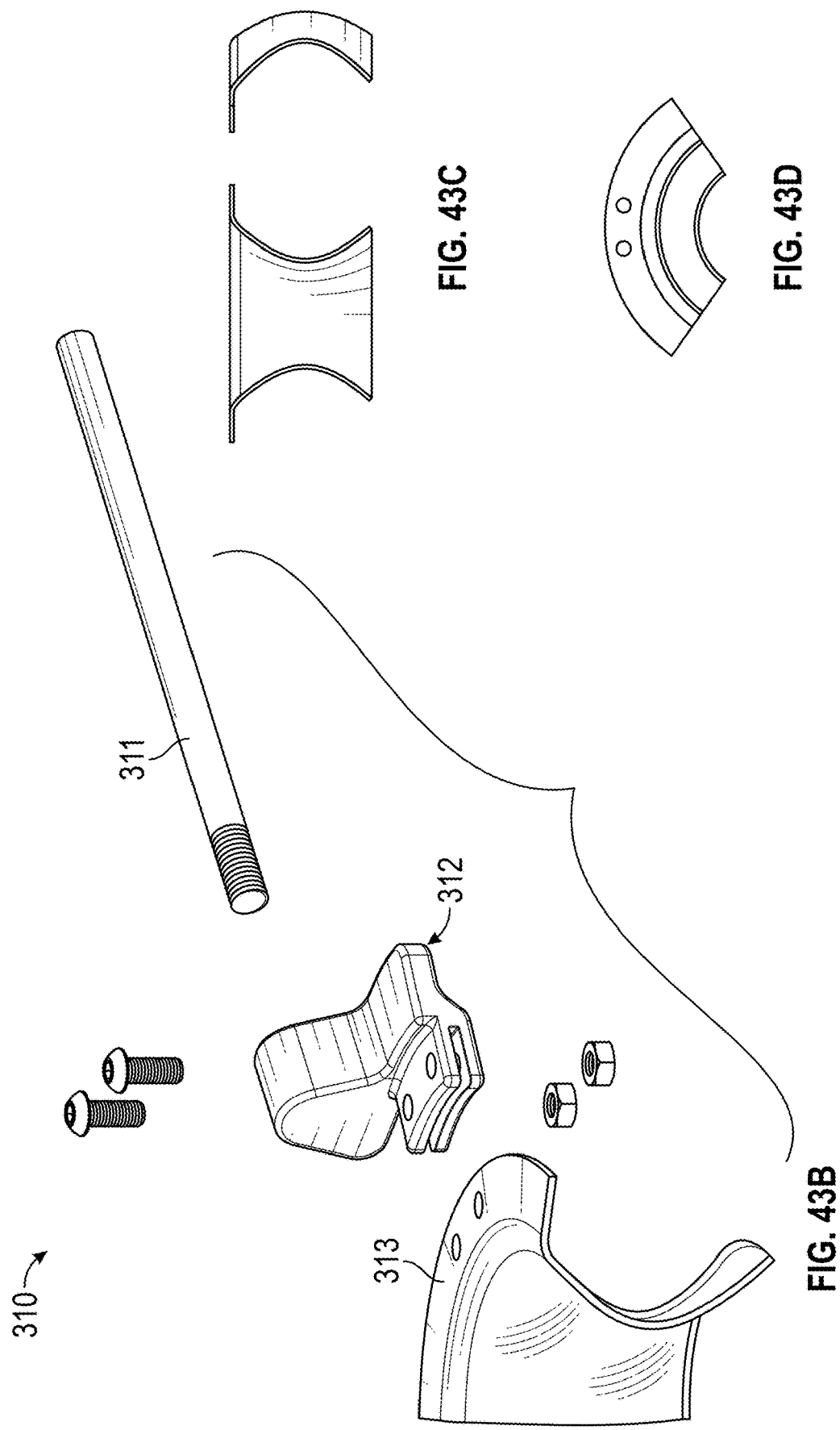

TISSUE EXTRACTION DEVICES AND RELATED METHODS

RELATED APPLICATIONS

The present patent application claims the benefit of priority to and is a continuation of International Application No. PCT/US2021/021444, filed Mar. 9, 2021, which claims the benefit of priority to U.S. Provisional Patent Application Ser. No. 63/138,441, filed Jan. 16, 2021, and U.S. Provisional Patent Application Ser. No. 62/987,345, Mar. 9, 2020. The present patent application is directed to similar subject matter to that disclosed in International Patent Application No. PCT/US17/68365, filed Dec. 23, 2017, which in turn claims the benefit of priority to U.S. Provisional Patent Application No. 61/438,916, filed Dec. 23, 2016, U.S. Provisional Patent Application No. 62/470,625, filed Mar. 13, 2017, and U.S. Provisional Patent Application No. 62/569,293, filed Oct. 6, 2017. This patent application is directed to similar subject matter to that disclosed in International Patent Application No. PCT/US2016/061595, filed Nov. 11, 2016, which in turn claims the benefit of priority to U.S. Provisional Patent Application No. 62/255,065, filed Nov. 13, 2015, and U.S. Provisional Patent Application No. 62/400,915, filed Sep. 28, 2016. Each of the foregoing patent applications is hereby incorporated by reference herein for any purpose whatsoever.

TECHNICAL FIELD

Various aspects of the present disclosure relate generally to surgical devices and methods. More specifically, the present disclosure relates to tissue extraction devices and related methods for minimally invasive surgery.

BACKGROUND

Conventional tissue extraction devices, such as laparoscopic morcellators, may include a sharp spinning blade for cutting tissue. Such devices may be inefficient and may require prolonged operating times, resulting in increased cost. Such devices also may cause unintended injuries. In some instances, conventional laparoscopic morcellators have the potential to spread occult malignancy, and this may worsen patient prognosis. Improving the design and operation of tissue extraction devices may address one or more of the aforementioned issues.

SUMMARY

Aspects of the present disclosure relate to, among other things, tissue extraction devices and related methods. Each of the aspects disclosed herein may include one or more of the features described in connection with any of the other disclosed aspects.

It may be understood that both the foregoing general description and the following detailed description are illustrative and explanatory only and are not restrictive of the features claimed.

As used herein, the terms "comprises," "comprising," or any other variation thereof, are intended to cover a non-exclusive inclusion such that a process, method, article, or apparatus that comprises a list of elements does not necessarily include only those elements, but may include other elements not expressly listed or inherent to such process, method, article, or apparatus.

The disclosure provides, among other things, embodiments of a tissue extraction device. In various embodiments, the device can include a bag made from a layer of material having an open proximal end and a closed distal end, wherein the bag defines an interior bounded by an inner surface, and at least one cutter extending through the interior of the bag along an inner surface of the bag. The at least one cutter includes a strand and at least one cutting element on the strand. The at least one cutting element includes a cutting edge to cut tissue as the cutter is drawn across tissue. In some implementations, the layer of material forming the bag can include at least one line of weakness (e.g., score lines and/or perforations) that in turn define at least one detachable section of the bag. That is to say, a portion of the bag that can be torn off. The at least one detachable section can be coupled to the at least one cutter such that the detachable section remains coupled to the cutter after the detachable section has been detached from the layer of material. If desired, the detachable section can actually be a portion of the wall of the bag.

The at least one cutter can include a plurality of cutters arranged parallel to each other, wherein each said cutter in the plurality of cutters remains coupled to the detachable section after the detachable section has been detached from the bag. The at least one cutter can include a plurality of cutters arranged parallel to each other, wherein each said cutter in the plurality of cutters remains coupled to the detachable section after the detachable section has been detached from the bag.

The tissue extraction device can further include a rolling ring, wherein a proximal portion of the bag is configured to be rolled around the rolling ring after the at least one detachable section has been detached from the bag. The rolling ring can include a ring body defining at least one protrusion to engage a portion of the bag. A proximal portion of the bag can define one or more holes to receive the at least one protrusion of the retractor ring after the at least one detachable section has been detached from the bag.

The tissue extraction device can further include a frame including at least one fastener to couple to and retain the rolling ring. The frame can define a downwardly depending wound protector that in turn can define a central opening therethrough to permit the passage of the cutter therethrough. The central opening can be bounded by or defined by a resilient bearing surface on a downwardly depending face thereof to act as a surface for the at least one cutter to bear against to prevent the at least one cutter from cutting the downwardly depending wound protector. The bearing surface can be made from an abrasion resistant material, such as a metal, a ceramic or a hard plastic, among others.

The rolling ring can be configured to permit a user to evert the rolling ring one or more times to induce tension on an inner layer of the bag so that the inner layer of the bag pulls a tissue specimen in the bag away from an outer layer of the bag and firmly hold onto the tissue specimen in preparation for cutting.

If desired, the wound protector can be removably coupled to the frame by way of at least one fastener. The frame includes at least one retractor detent to receive a retractor arm of a retractor. If desired, the frame can include a plurality of retractor detents, each said retractor detent being configured to receive a retractor arm of a retractor, wherein edges of retractor blades disposed on the retractors overlap one another in an open central region of the frame to cooperatively form an annulus proximate an incision in a patient. The tissue extraction device can include a plurality of cutters extending through the interior of the bag along the inner surface of the bag, and further wherein each of the plurality of cutters is associated with indicia indicative of an order of progression for using each cutter. The indicia can be coupled to the detachable section of the bag, for example. In various embodiments, the tissue extraction device can further include an outer bag surrounding the bag.

The disclosure also includes methods of extracting tissue. In some embodiments, the methods can include inserting a bag into a patient via an incision, inserting a tissue specimen through an opening of the bag into a cavity defined by an inwardly facing surface of the bag, withdrawing a portion of the bag through the incision, detaching at least one detachable section of the bag from the bag, coupling a remaining portion of the bag withdrawn through the incision to a rolling ring, rolling at least a portion of the bag at least partially around the rolling ring so that the rolling ring is at least partially surrounded by the bag, wherein the tissue specimen is drawn toward the incision and held in place by tension imparted by the bag being rolled at least partially about the rolling ring, cutting through the tissue specimen with at least one elongate flexible cutter disposed proximate the tissue specimen in a reciprocating sawing motion.

In some implementations, the cutting step can be performed by detaching the at least one elongate flexible cutter from an inner surface of the bag, the at least one elongate flexible cutter having a first end and a second end, withdrawing the first end and second end of the at least one elongate flexible cutter from the patient through said opening to the bag and the rolling ring, and pulling the at least one elongate flexible cutter back and forth causing the at least one elongate flexible cutter to cut through said tissue specimen.

In some implementations, the cutting step can include pulling each of a plurality of elongate flexible cutters back and forth through said tissue specimen individually in a predetermined sequence.

The method can further include coupling the rolling ring to a frame after the rolling step, so that the frame is coupled to the rolling ring and the bag, and guiding the at least one elongate flexible cutter through at least one guide channel defined by the frame.

The disclosure also provides a tissue extraction device that includes a bag made from a layer of material having an open proximal end and a closed distal end, the bag defining an interior bounded by an inner surface, and at least one cutter extending through the interior of the bag along an inner surface of the bag, wherein the at least one cutter includes a first strand and a second strand coupled to at least one blade, wherein the at least one blade includes at least one cutting edge to cut tissue as the at least one cutter is drawn across tissue.

If desired, the at least one blade can be removably attached to the inner surface of the bag at a location displaced from the closed distal end of the bag. The at least one cutter can include a plurality of individual cutters arranged parallel to each other, wherein the at least one blade of adjacent cutters are located on opposing sides of the inner surface of the bag. The system can further include a rolling ring, wherein a proximal portion of the bag is configured to be rolled around the rolling ring. The rolling ring can include a ring body defining at least one protrusion to engage a portion of the bag. If desired, a proximal portion of the bag can define one or more openings therethrough to receive the at least one protrusion of the retractor ring after the at least one detachable section has been detached from the bag.

In some implementations, the at least one blade is held in place against the inner wall of the bag within a blade holder subassembly. The first strand and second strand can be surrounded by a tubular member to facilitate sliding of the at least one cutter along the inner surface of the bag.

The tissue extraction device can further include a frame including at least one fastener to retain the rolling ring after a proximal portion of the bag has been rolled about the rolling ring. The first strand and second strand of the at least one cutter can be about the same length. The first strand can extend from the open proximal end of the bag further than the second strand extends from the open proximal end of the bag.

Where provided, a plurality of cutters can traverse a path along the inner surface of the bag parallel to one another along the closed distal end of the bag and that converge as the plurality of cutters approach the open proximal end of the bag. The plurality of cutters can be received by a retainer coupled to the inner surface of the bag after the paths of the cutters have converged.

In some implementations, the frame can include at least one retractor arm of a retractor, wherein the at least retractor arm is aligned with a direction that does not pass through a geometric center of the frame to permit the at least one cutter to pass over the frame along a direction parallel to a line that passes through the geometric center of the frame. The at least one retractor arm can include a plurality of retractor arms. Each of the plurality of retractor arms can include a retractor blade disposed at a radially inner end thereof, wherein edges of adjacent retractor blades disposed on the retractors overlap one another in an open central region of the frame to cooperatively form an annulus proximate an incision in a patient.

The disclosure provides further methods of extracting tissue. In some implementations, the method includes inserting a bag into the patient via an incision, inserting a tissue specimen through an opening of the bag into a cavity defined by an inwardly facing surface of the bag, and withdrawing a portion of the bag through the incision. The method can further include coupling an open proximal end of the bag withdrawn through the incision to a rolling ring, rolling at least a portion of the bag at least partially around the rolling ring so that the rolling ring is at least partially surrounded by the bag, wherein the tissue specimen is drawn toward the incision and held in place by tension imparted by the bag being rolled at least partially about the rolling ring. The method can still further includes cutting through the tissue specimen with at least one elongate flexible cutter disposed proximate the tissue specimen in a reciprocating sawing motion, wherein a blade of the at least one elongate flexible cutter is initially removably attached to the inner surface of the bag at a location displaced from a closed distal end of the bag.

In some implementations, the cutting step can be performed by detaching the at least one elongate flexible cutter from the inner surface of the bag by applying tension to a first end of at least one elongate flexible cutter that extends from the bag a lesser amount than a second end of the at least one elongate flexible cutter. The cutting step can include pulling each of a plurality of elongate flexible cutters back and forth through said tissue specimen individually in a predetermined sequence.

The method can further include coupling the rolling ring to a frame after the rolling step, so that the frame is coupled to the rolling ring and the bag; and guiding the at least one elongate flexible cutter through at least one guide channel defined by the frame. The method can further include coupling a plurality of retractor arms to the frame, each of the plurality of retractor arms including a retractor blade disposed at a radially inner end thereof, wherein edges of adjacent retractor blades disposed on the retractors overlap one another in an open central region of the frame to cooperatively form an annulus proximate an incision in a patient.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The accompanying drawings, which are incorporated in and constitute a part of this specification, illustrate aspects of the present disclosure and together with the description, serve to explain the principles of the disclosure.

FIG. 35 is a schematic view of a cutter in accordance with the present disclosure.

FIGS. 36A-37C illustrate further aspects of the cutter of FIG. 35.

DETAILED DESCRIPTION

The present disclosure is drawn to laparoscopic tissue devices and related methods. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject. The term "approximately," when used to describe a numerical value, may be anywhere in a range of ±5% from the numerical value.

Figure 1:
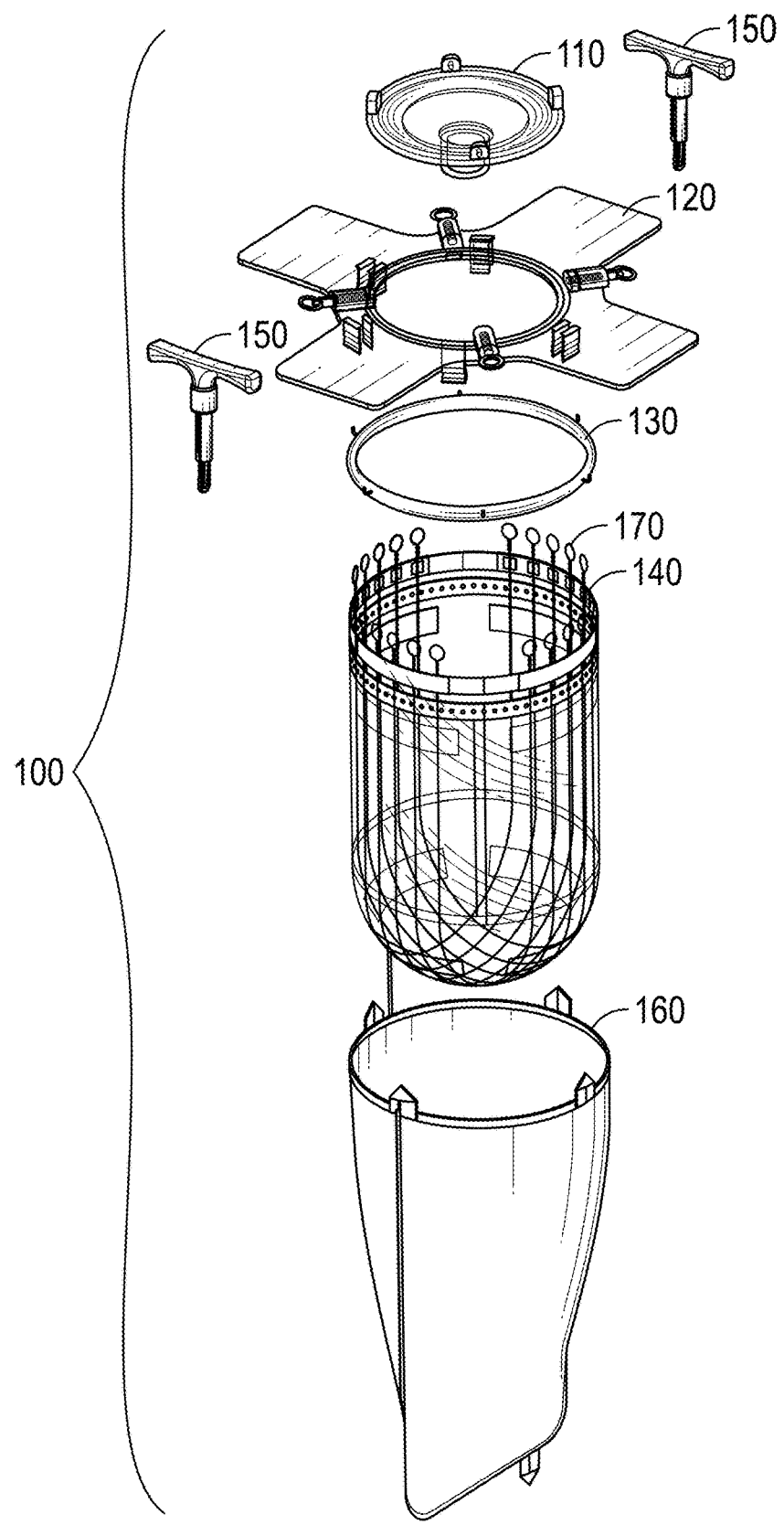
FIG. 1 is a first isometric shaded rendering in exploded view of a tissue extraction device in accordance with aspects of the present disclosure.

For purposes of illustration, and not limitation, a tissue extraction system 100 is illustrated in FIG. 1 in an exploded view. FIG. 1 illustrates sub components of the system 100, including a bag 140 to receive a tissue sample to be dissected, which in turn is configured to be coupled to a rolling ring 130. The ring 130 is configured to be received by an underside of frame 120. Frame 120 is configured to removably receive a wound protector disc 120 by way of one or more fasteners 190 that are spring loaded into frame 120. Bag 140 includes a plurality of cutters 170 configured to be coupled to gripping handle hooks 150. An outer bag 160 can be provided to capture any fluids or tissues not contained by bag 140 during the tissue dissection and removal process.

Figure 12:
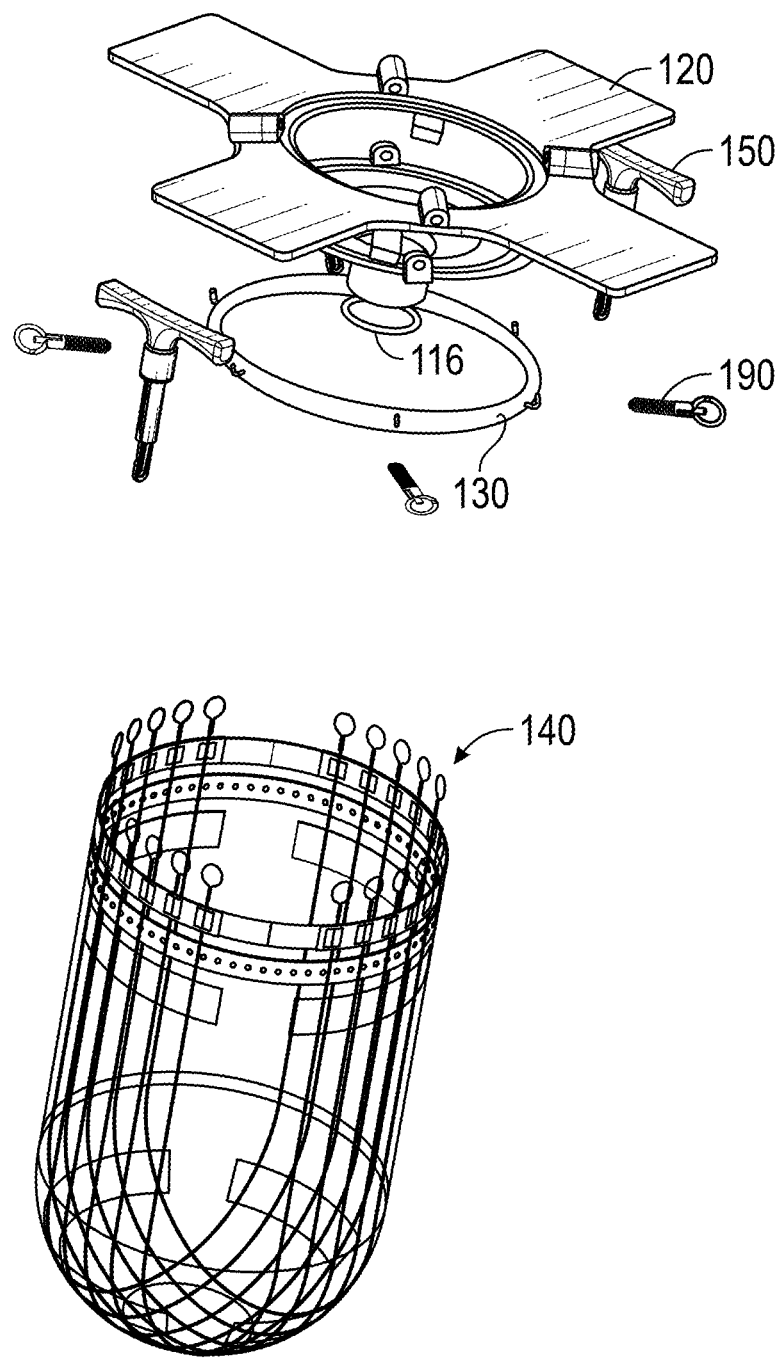
FIG. 12 is an isometric exploded line drawing view of a tissue extraction device in accordance with certain aspects of the present disclosure.
Figure 13:
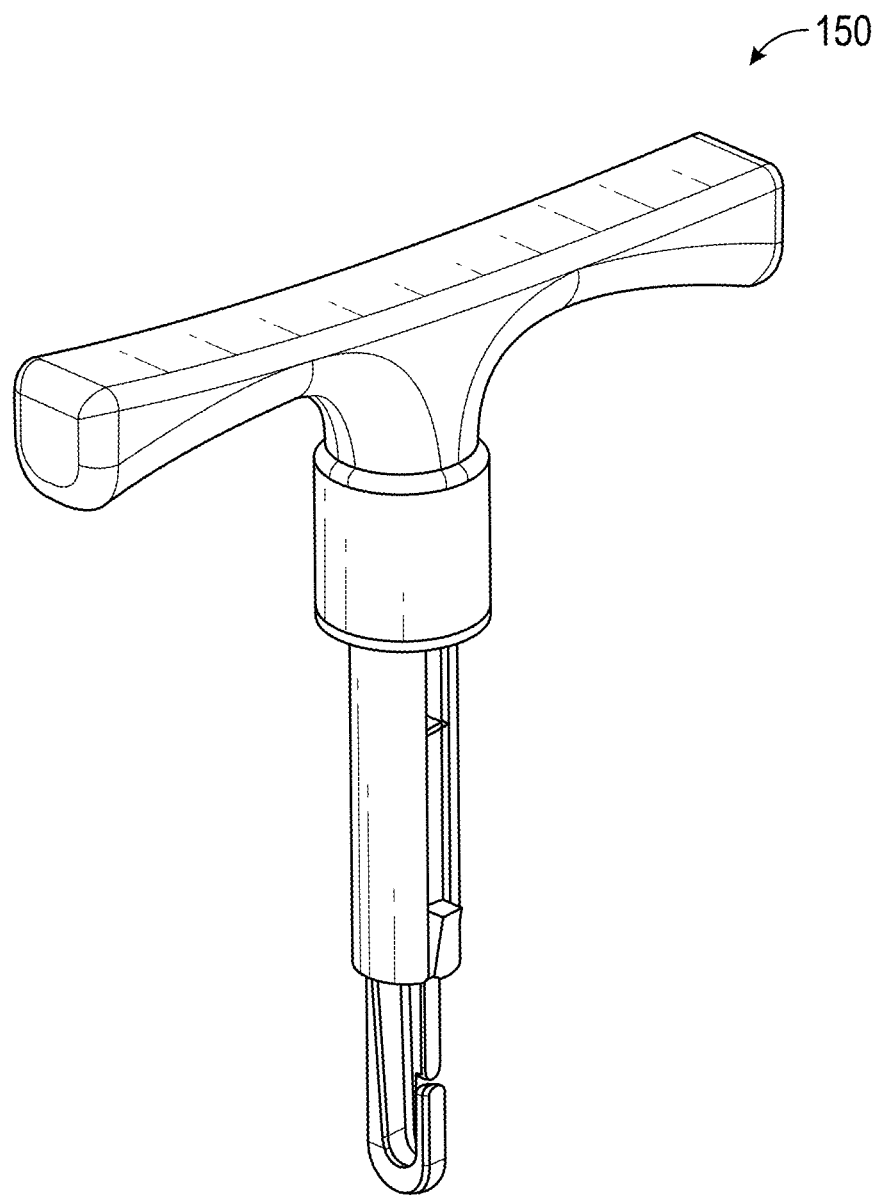
FIG. 13 is an isometric line drawing of an illustrative handle for coupling to a cutter in accordance with aspects of the present disclosure.
Figure 19:
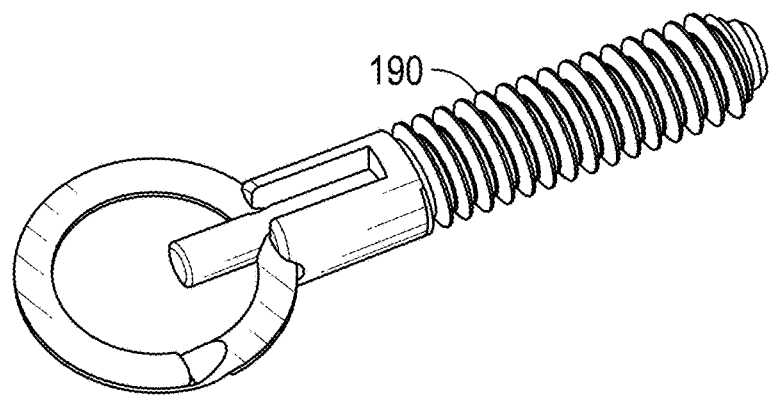
FIG. 19 is an isometric view of a fastener in accordance with aspects of the present disclosure.

As mentioned above, device 100 includes bag rolling ring 130. Bag rolling ring 130 is removably coupled to frame 120 via at least one fastener 190 (FIGS. 12, 19). Bag rolling ring 130 can include at least one hook 132 to which the bag 140 can be coupled. For example, bag rolling ring 130 can include pins, posts, bosses, and/or clips to couple bag 140 or a different bag to bag rolling ring 130. Bag rolling ring 130 is used to roll the bag 140 around bag rolling ring 130 as described below. Bag rolling ring 130 is made from a material with a firmness sufficient to prevent buckling during rolling the bag and to maintain optimal tension on a tissue specimen inside the bag.

Figure 2:
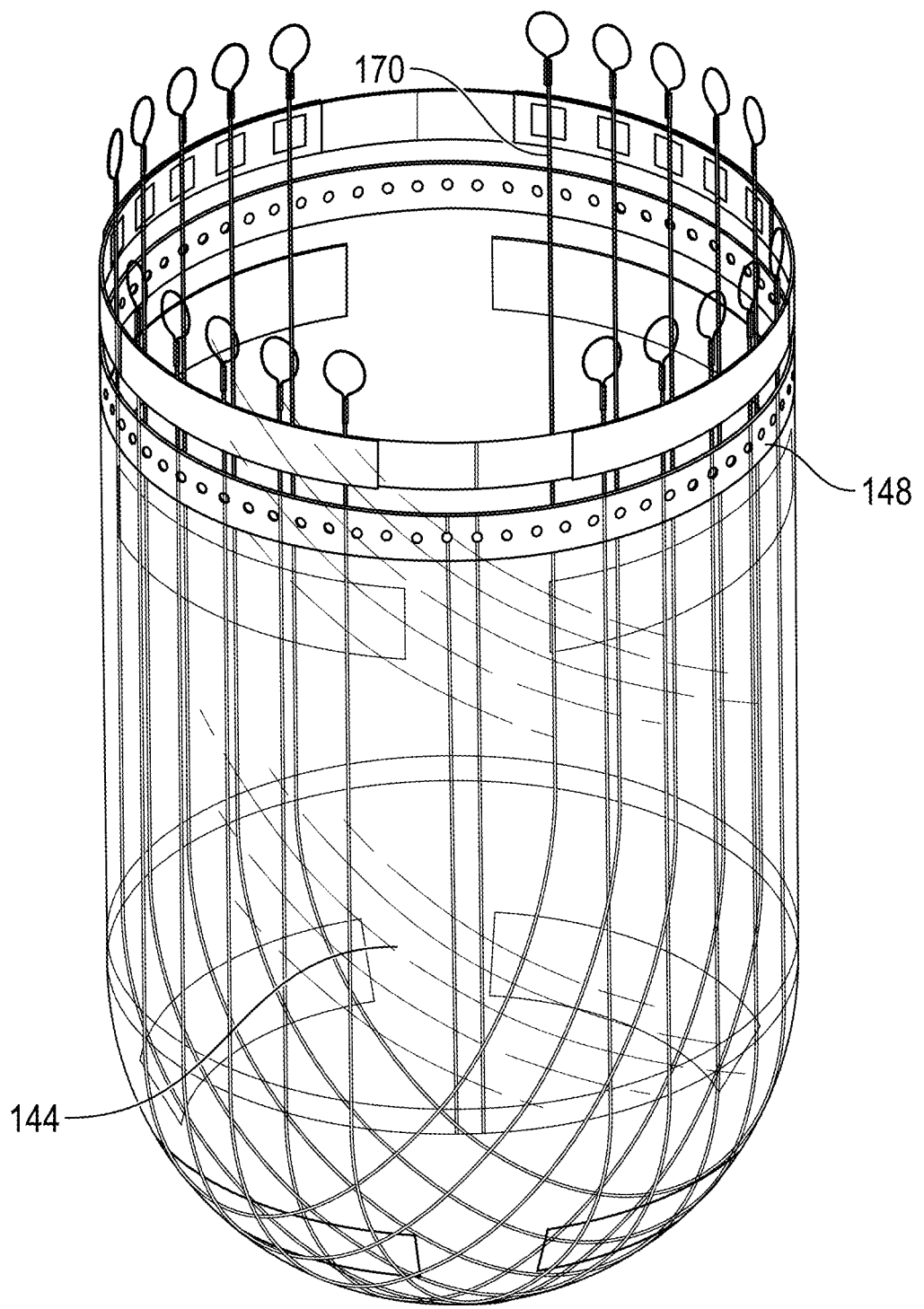
FIG. 2 is an isometric shaded rendering of a bag of the tissue extraction device of FIG. 1.
Figure 3:
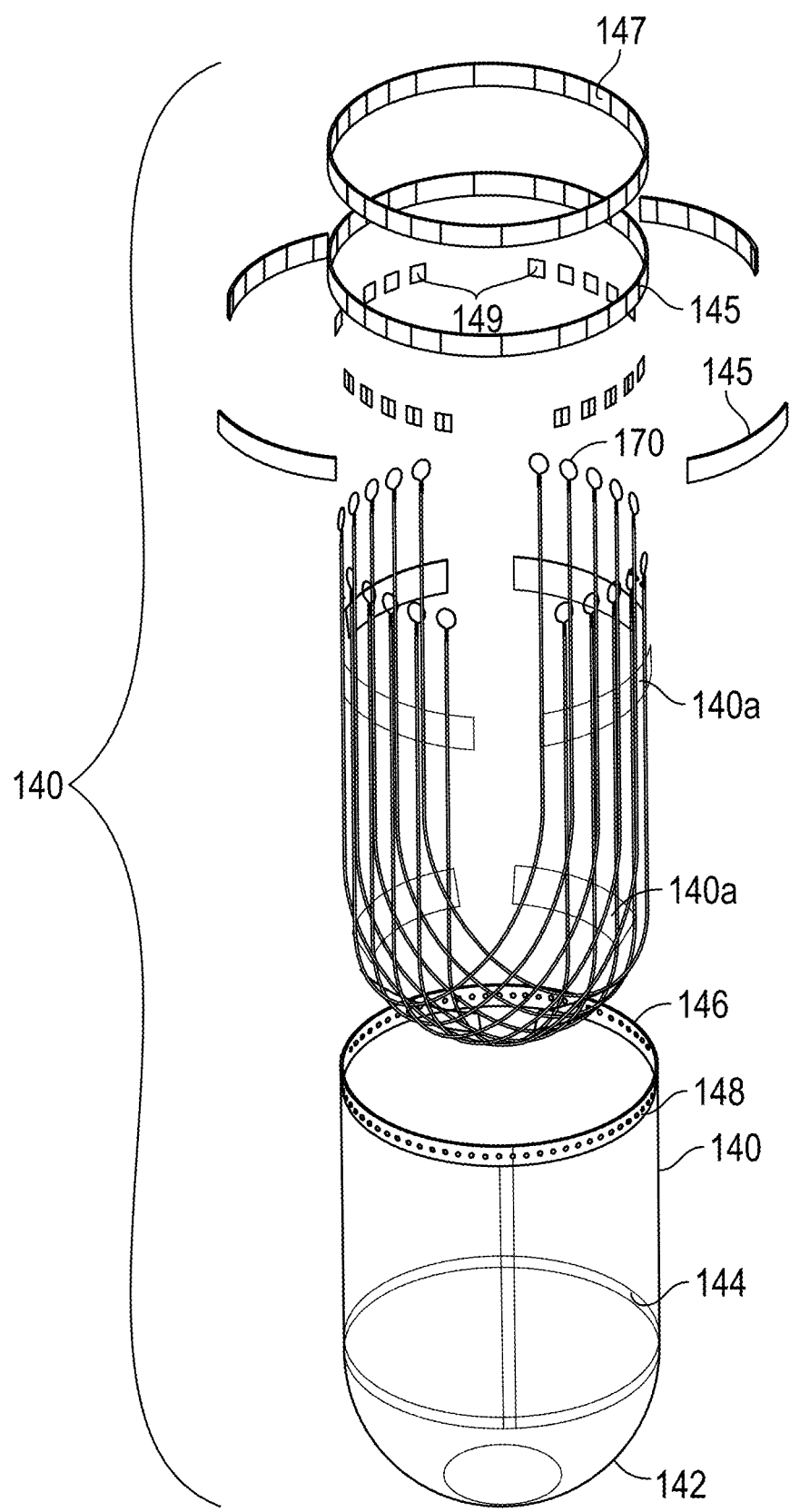
FIG. 3 is an exploded view of the bag of FIG. 2.
Figure 4:
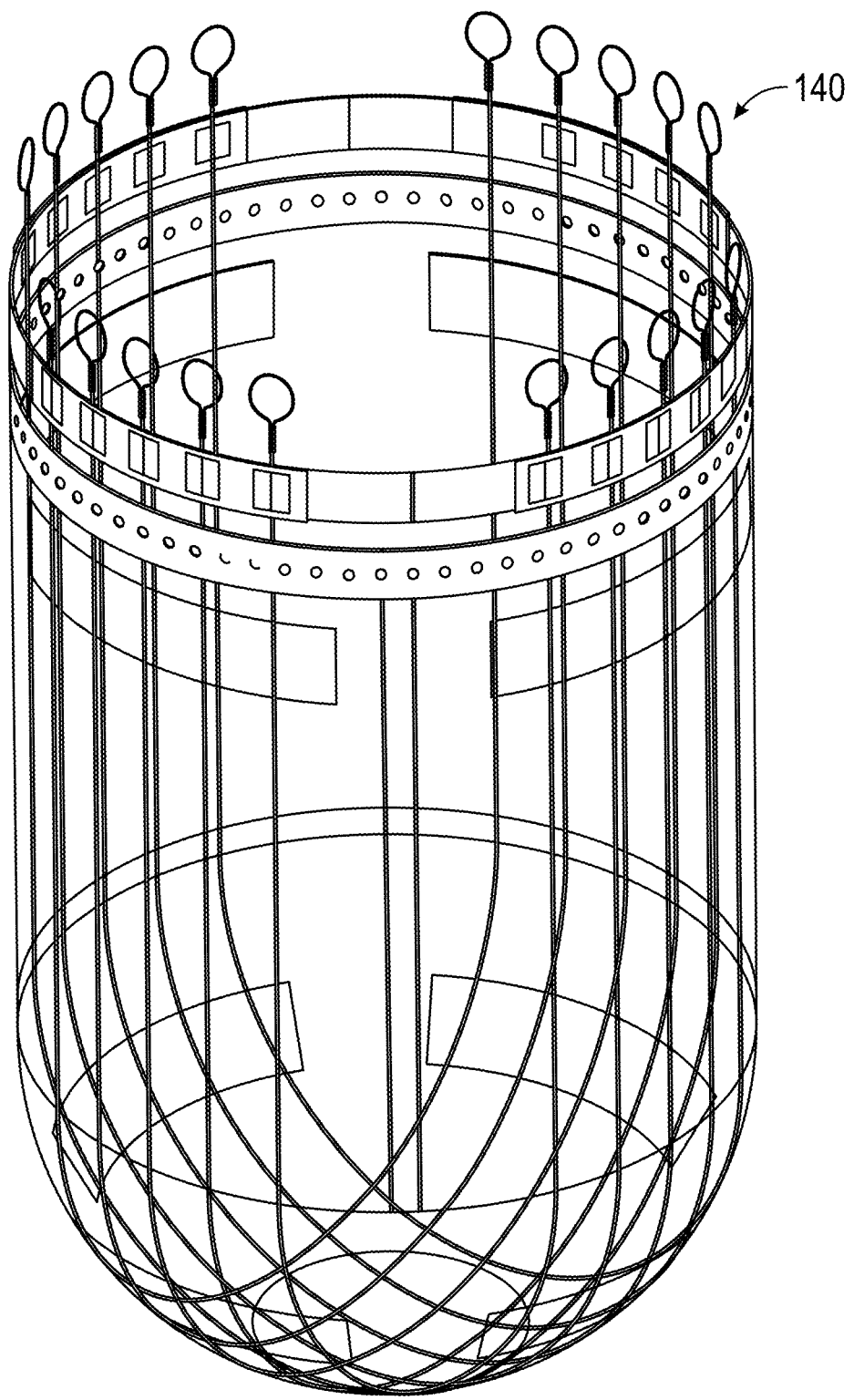
FIG. 4 is an isometric black and white line drawing of a bag of the tissue extraction device of FIG. 1.
Figure 5:
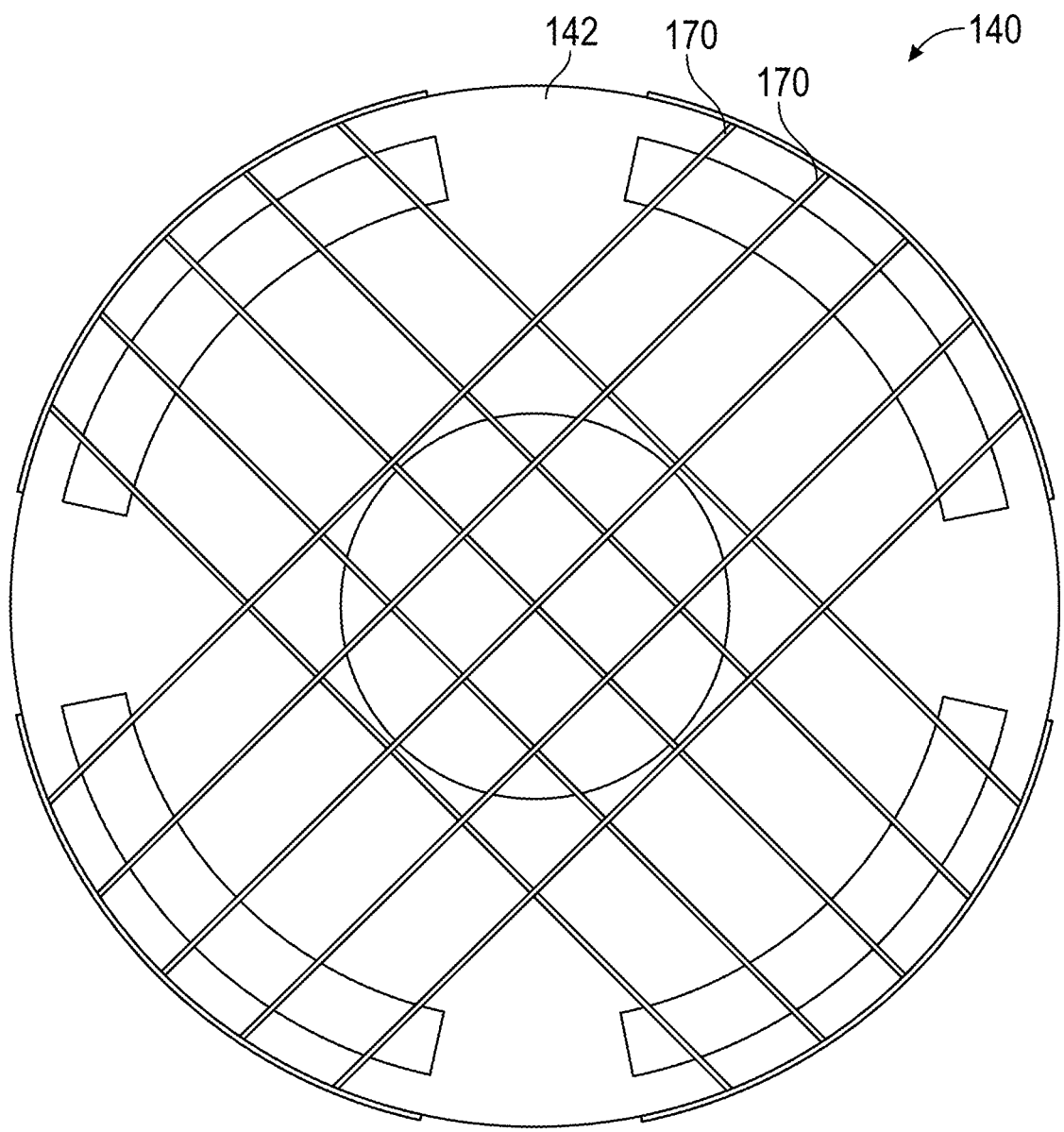
FIG. 5 is a line drawing of a bottom view of the bag of FIG. 2.
Figure 6:
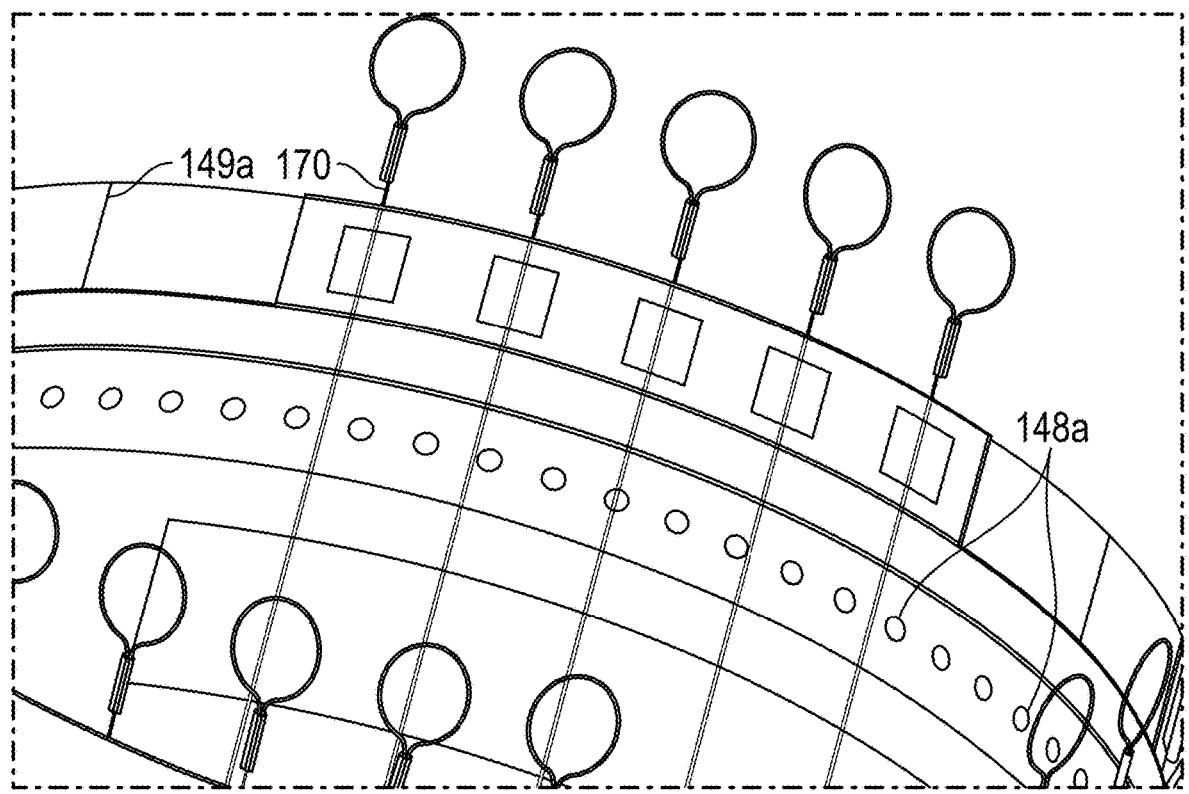
FIG. 6 is an isometric view of a portion of the black and white line drawing of FIG. 6.
Figure 7:
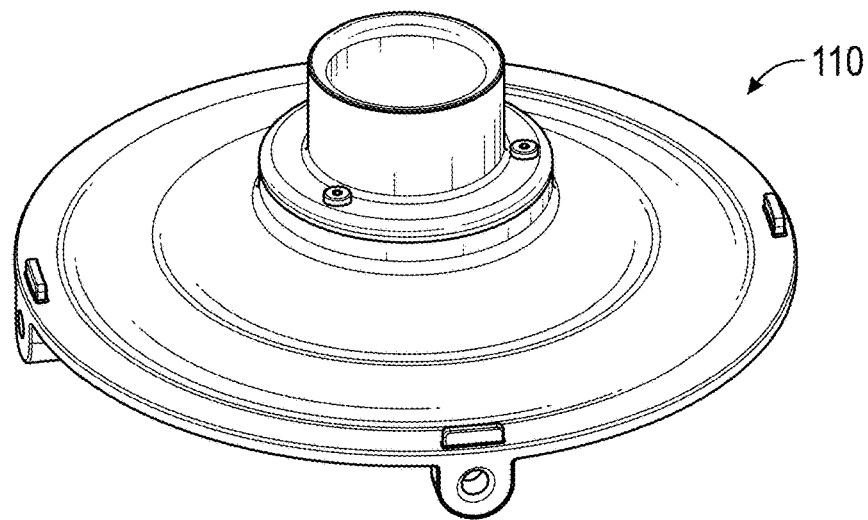
FIG. 7 is an isometric view of a wound protector disc of the tissue extraction device of FIG. 1.

FIG. 2 is an isometric shaded rendering of a bag of the tissue extraction device of FIG. 1. FIG. 3 is an exploded view of the bag of FIG. 2. FIG. 4 is an isometric black and white line drawing of a bag of the tissue extraction device of FIG. 1. FIG. 5 is a line drawing of a bottom view of the bag of FIG. 2. FIG. 6 is an isometric view of a portion of the black and white line drawing of FIG. 6. As illustrated, bag 140 includes a sidewall 144 that is coupled to a bottom portion 142 that cooperate to surround a volume. As illustrated, a row 148 of perforations 148a or other line of weakness can be fractured or torn so as to separate upper tear-away sections 145, 147 from the bag 140. The tear away sections are coupled to the proximal end regions of cutters 140 so as to permit the cutters to be advanced out of a wound and into couplings on frame 120 or disc 110, illustrated in further detail below. Indicia tabs 149 can be placed over each cutter and couple each cutter to the tear away sections 145, 147, as desired. Tapes or layers of material 140a can be provided that are attached to sidewall 144 or lower portion 142 to help hold cutters 170 in place as the bag 140 is being installed and populated with a tissue specimen to be dissected.

Figure 8:
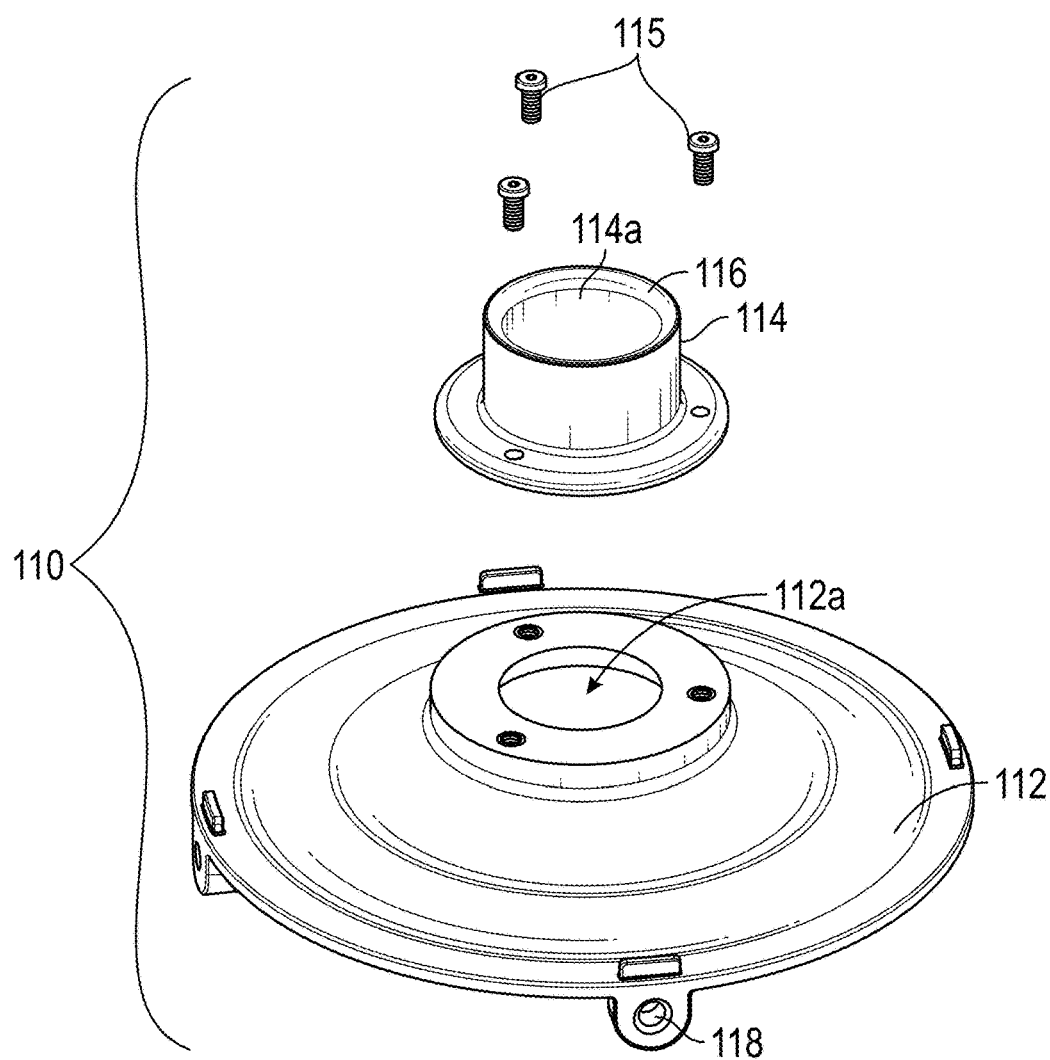
FIG. 8 is an isometric exploded view of the wound protector disc of FIG. 7.
Figure 9:
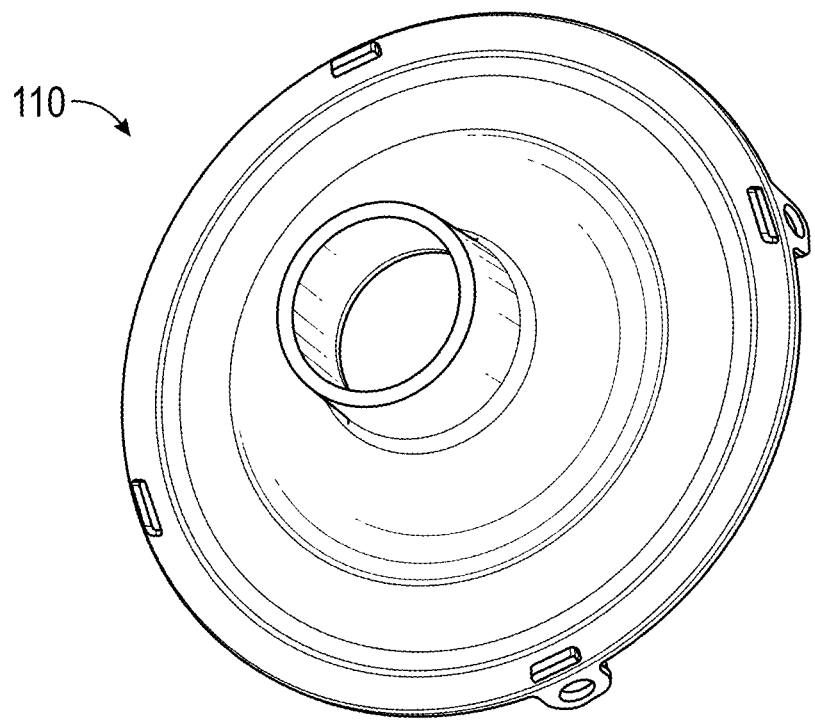
FIG. 9 is a top isometric view of the wound protector disc of FIG. 7.
Figure 10:
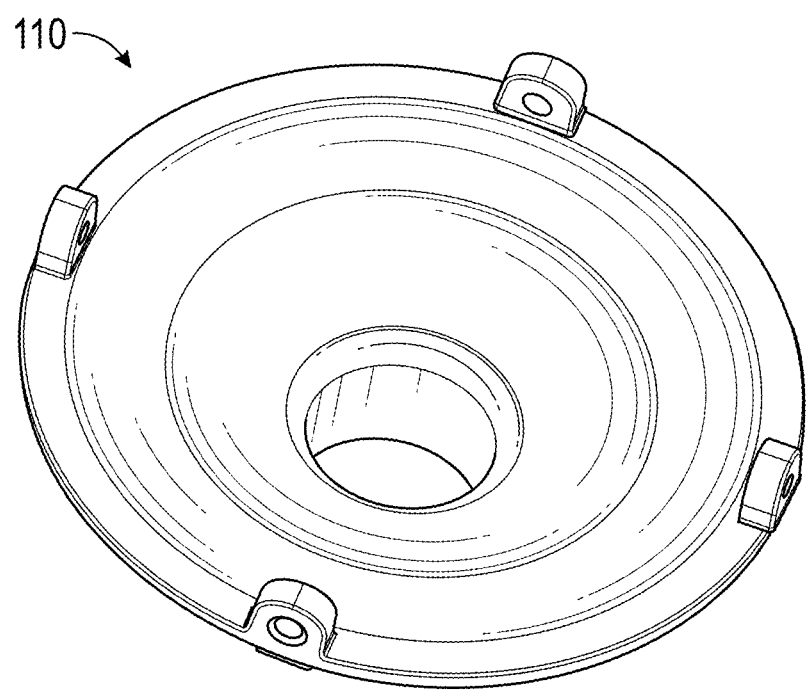
FIG. 10 is a bottom isometric view of the wound protector disc of FIG. 7.
Figure 11:
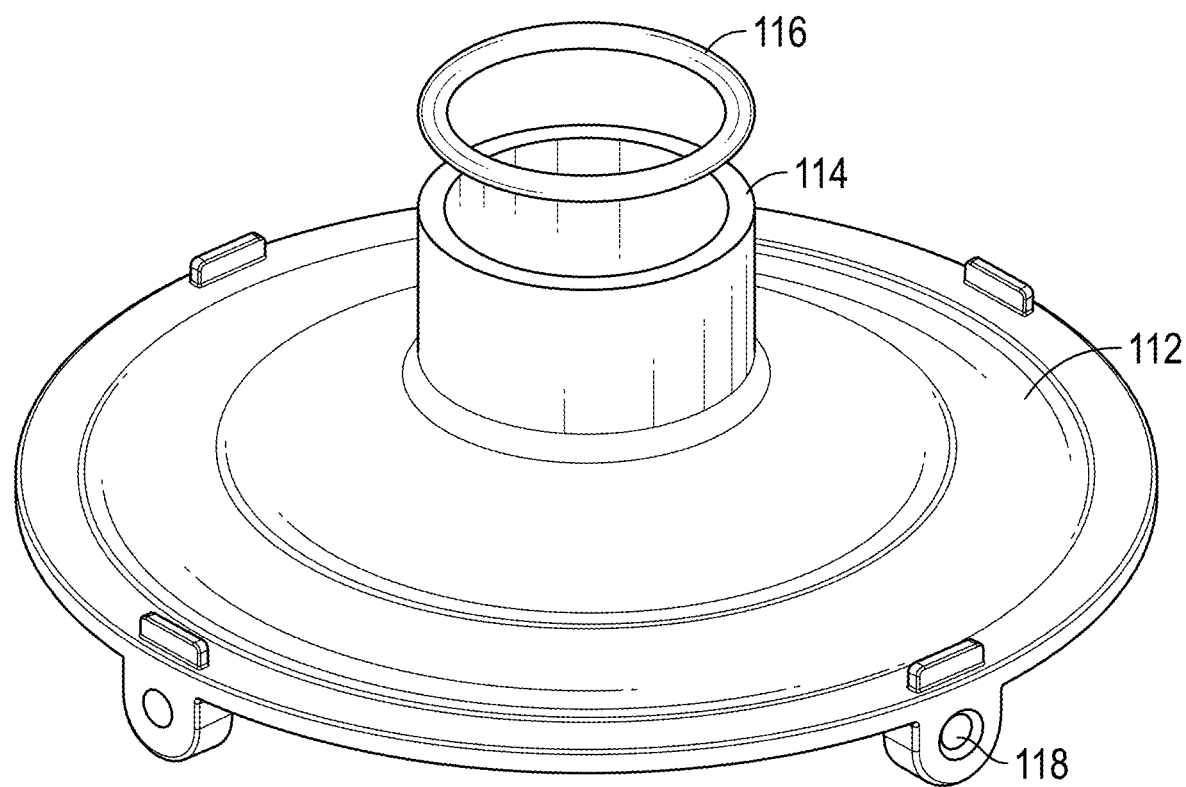
FIG. 11 is a top partially exploded view of the wound protector disc of FIG. 7.

FIGS. 7-11 show a first embodiment of a wound protector disc of the tissue extraction device of FIG. 1. The disc 110 includes a disc body 112 that is coupled to or integral with wound protector sleeve 114 and hardened or resilient bearing surface 116. FIG. 8 illustrates that sleeve 114 can be coupled to disc 112 by way of one or more fasteners 115.

Figure 14:
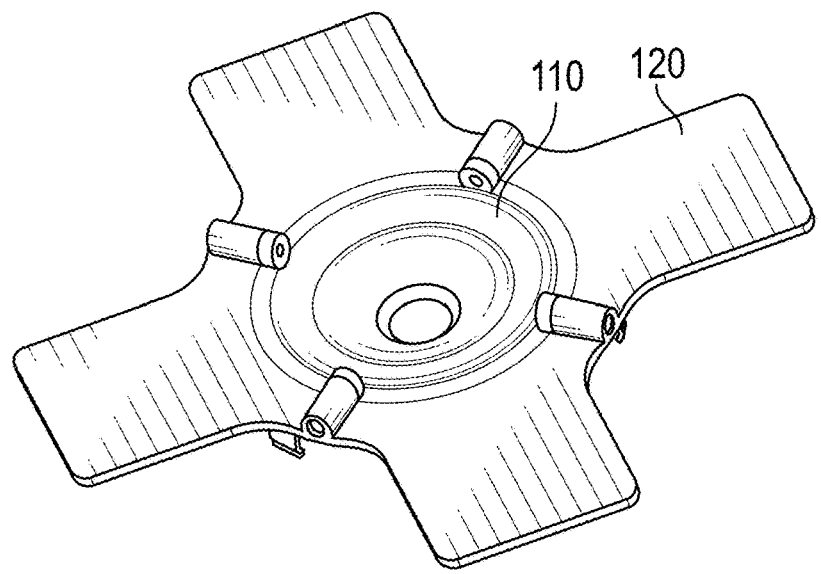
FIG. 14 is a top isometric view of a frame and wound protector disc in accordance with the present disclosure.
Figure 15:
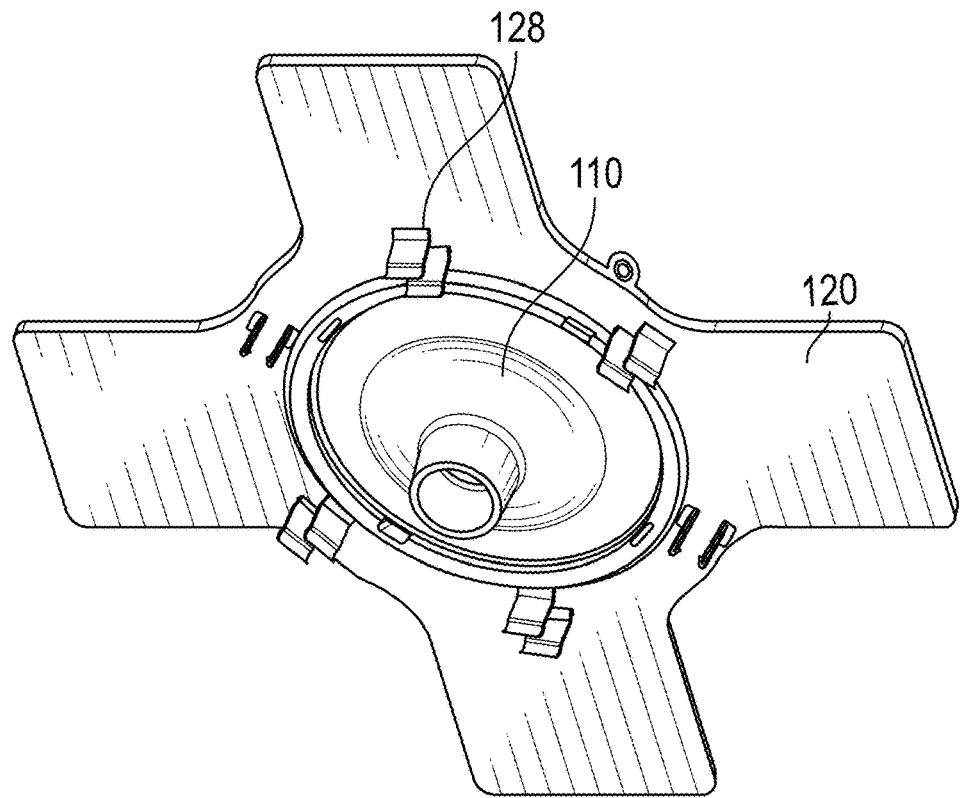
FIG. 15 is a bottom isometric view of the structure illustrated in FIG. 14.
Figure 16:
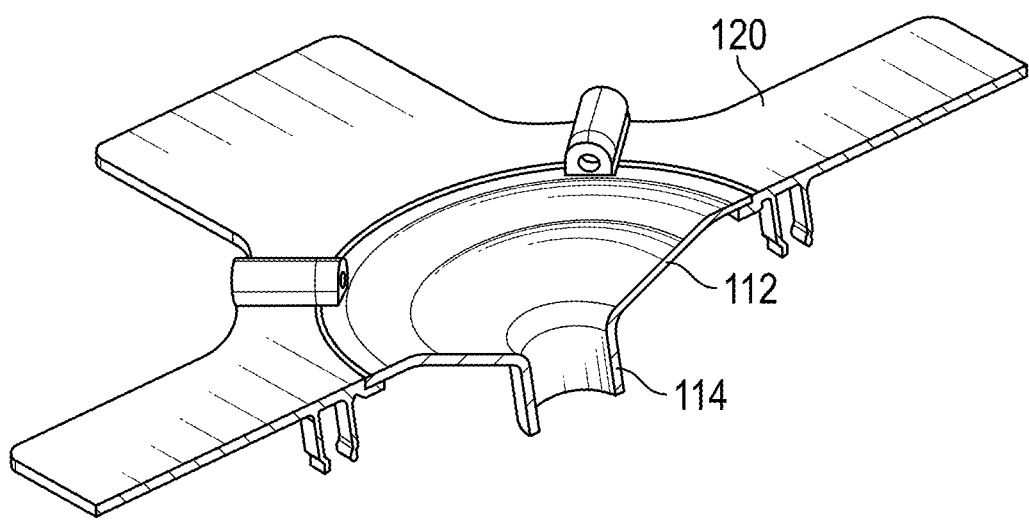
FIG. 16 is a cross-sectional view of the structure illustrated in FIG. 14.

FIGS. 14-15 are top and bottom isometric views of a frame and wound protector disc in accordance with the present disclosure. As illustrated, the frame and disc can be coupled to one another by way of fasteners 190. Fasteners 128, which are illustrated as being integral with frame 120, can be snap fit over rolling ring 130 after the upper open portion of the bag 140 is rolled around the ring 130. FIG. 16 illustrates the cross-sectional profile of the assembly of FIGS. 14-15.

Figure 17:
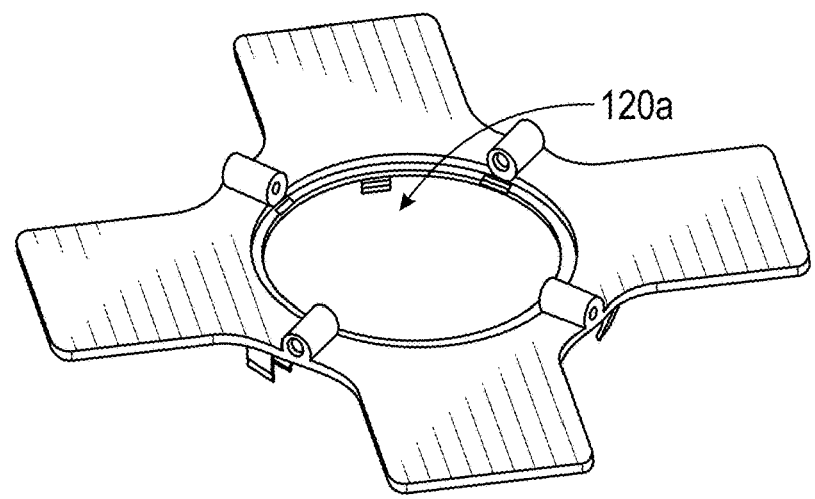
FIG. 17 is a top isometric view of the frame of FIG. 14 with the wound protector disc removed in accordance with the present disclosure.
Figure 18:
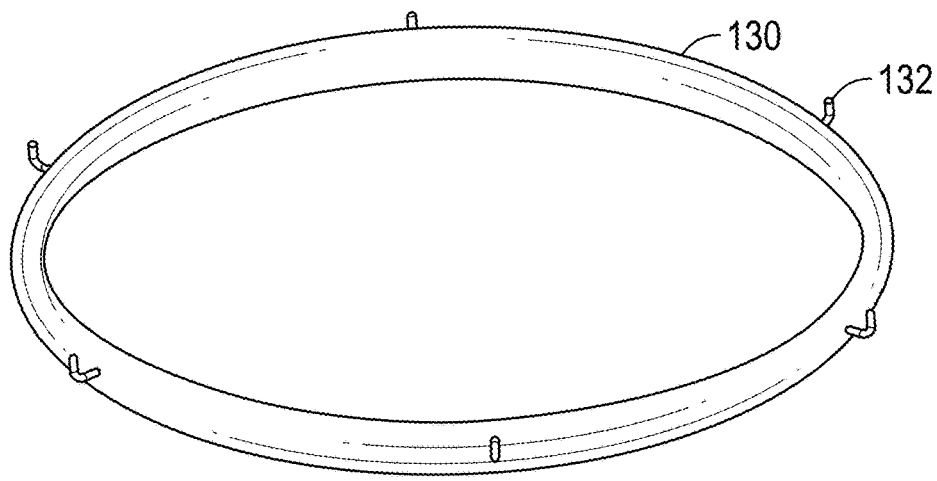
FIG. 18 is an isometric view of a rolling ring in accordance with aspects of the present disclosure.

FIG. 17 illustrates the frame 120 without the disc 110 disposed in opening 120a of the frame 120. FIG. 18 illustrates the rolling ring 130, including a plurality of hooks 132 to engage with perforations 148a in bag 140.

Figure 20:
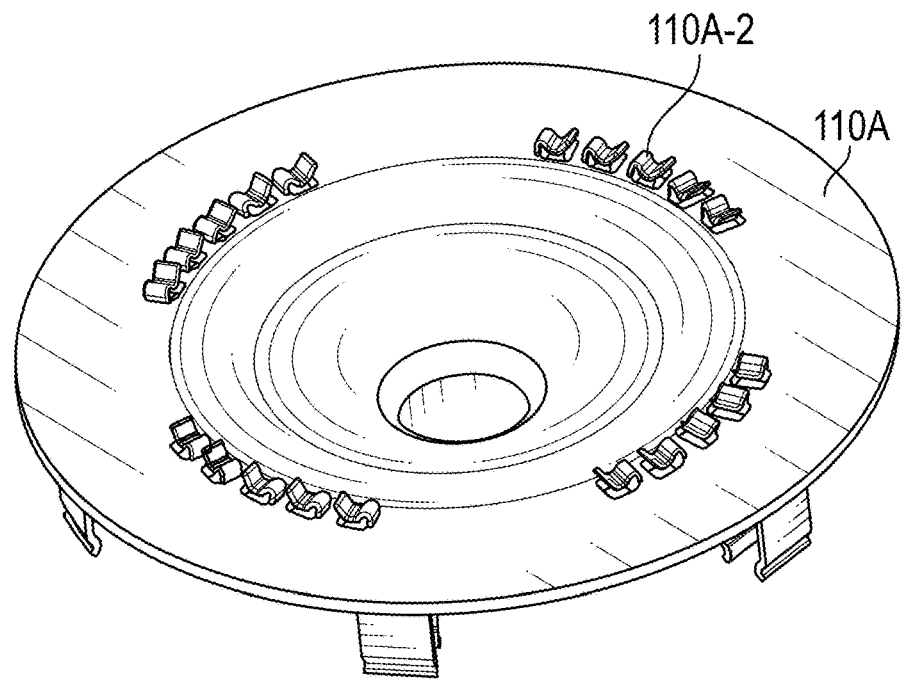
FIGS. 20-22 are views of further embodiments of wound protector discs in accordance with aspects of the present disclosure.
Figure 21:
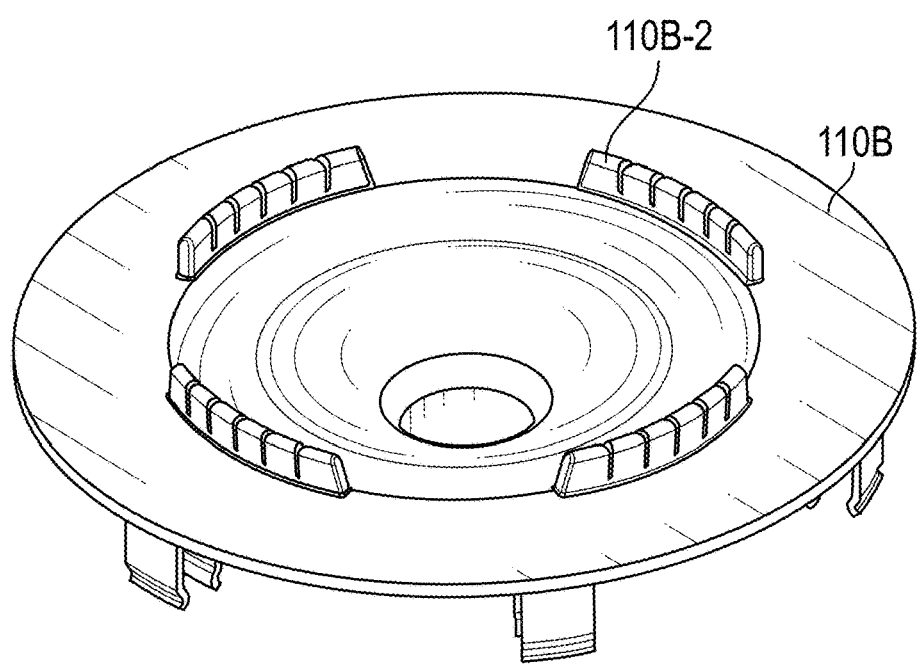
Figure 22:
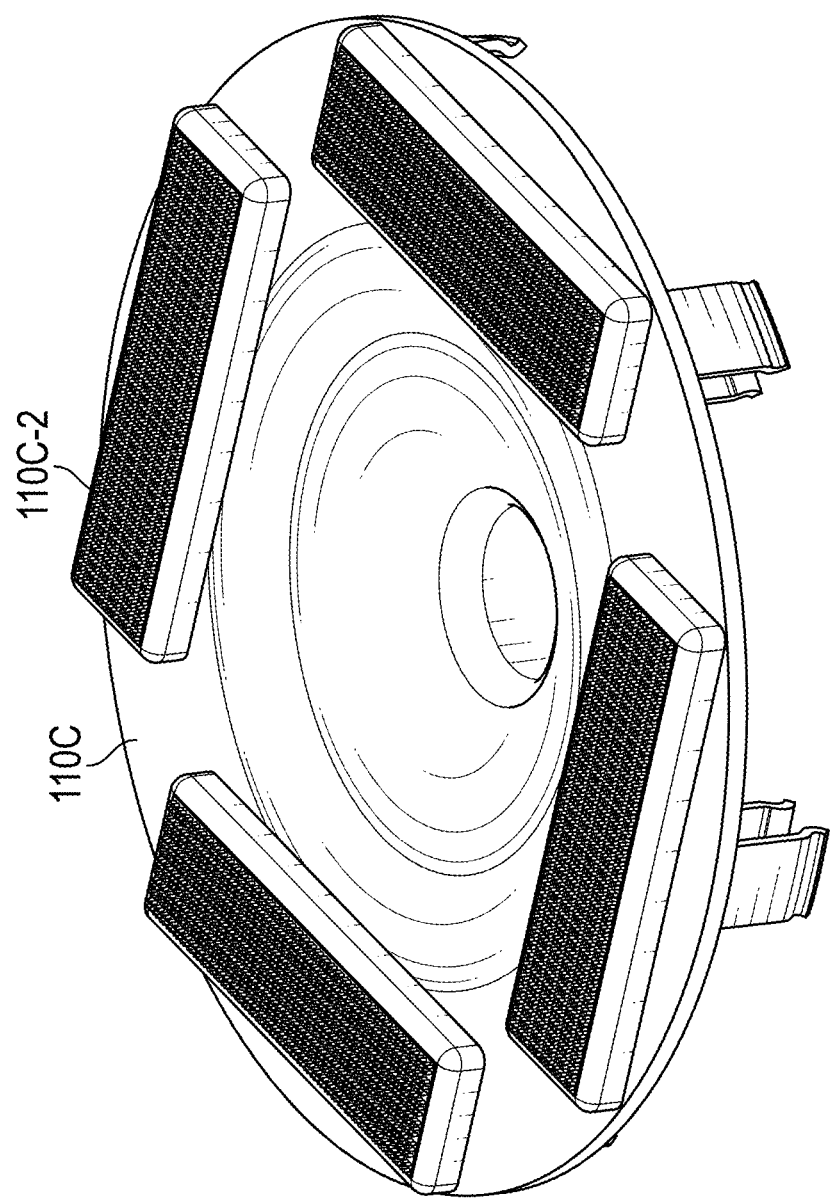

FIGS. 20-22 are views of further embodiments of wound protector discs in accordance with aspects of the present disclosure. Specifically, FIG. 20 shows a disc 110A that in turn defines four sets of retainer clips 110A-2 to retain the free ends of the cutters 170. FIG. 21 illustrates a variant 110B that includes retainer grooves to retain the free ends of the cutters 170. FIG. 22 illustrates a further variant 110C that in turn includes patches of hook and loop fastener 110C-2 in order to retain the free ends of cutters 170.

Figure 23:
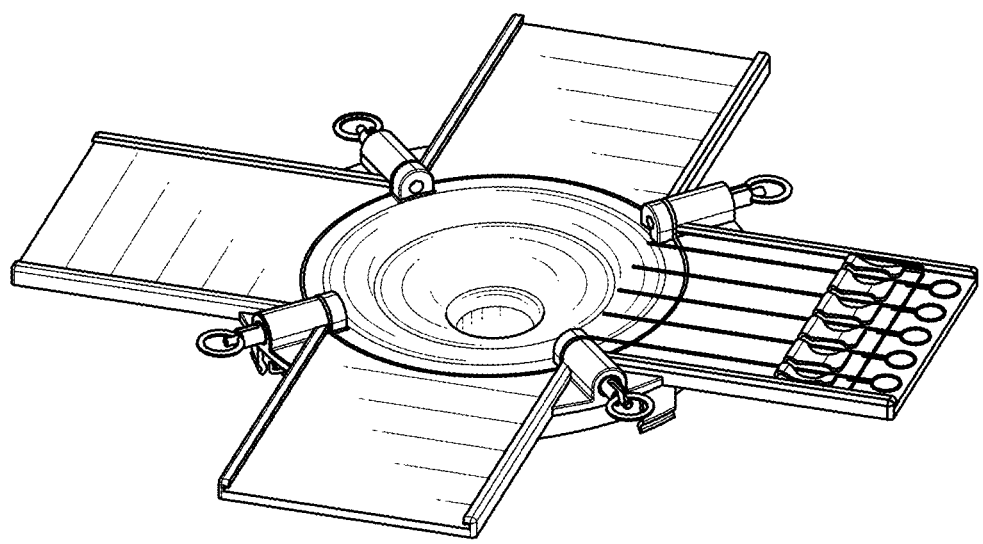
FIGS. 23 and 24 are assembled and exploded views of a frame and wound protector disc in accordance with the present disclosure.
Figure 24:
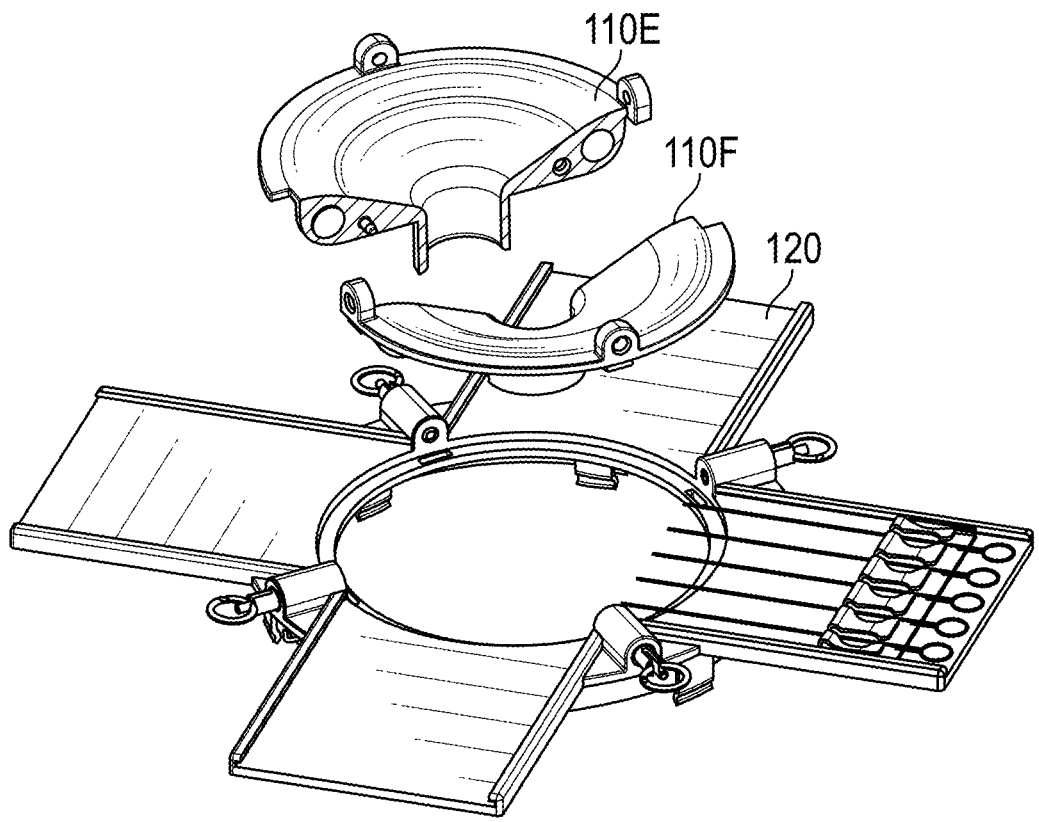

FIGS. 23 and 24 are assembled and exploded views of a frame and wound protector disc in accordance with the present disclosure. In this implementation, the wound protector disc is separable into two halves 110E, 110F.

Figure 25:
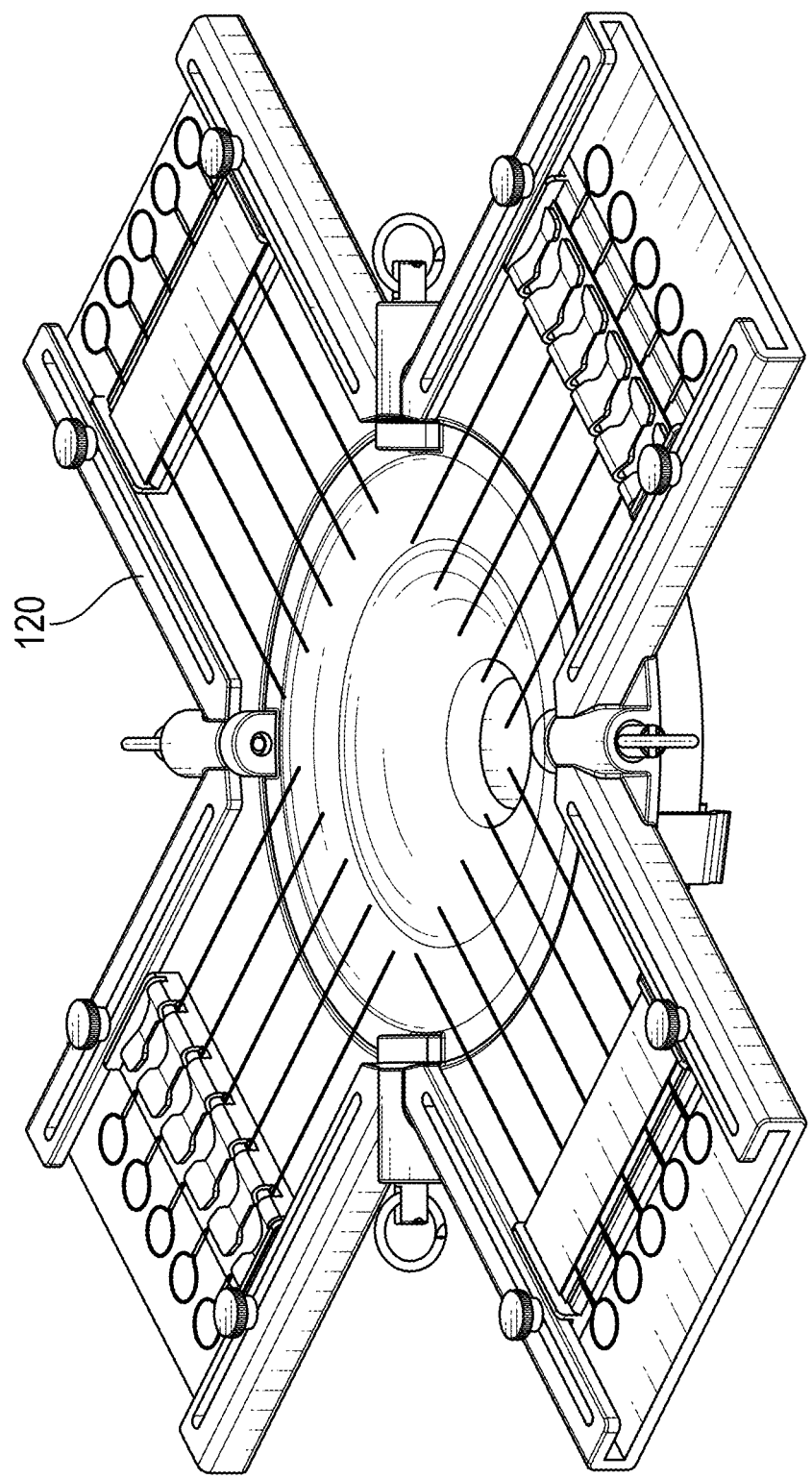
FIG. 25 is an assembled view of a frame and wound protector disc in accordance with the present disclosure showing the relative placement of cutters on the frame prior to initiating a dissection procedure.

FIG. 25 is an assembled view of a frame and wound protector disc in accordance with the present disclosure showing the relative placement of cutters 170 on the frame 120 prior to initiating a dissection procedure.

Figure 26:
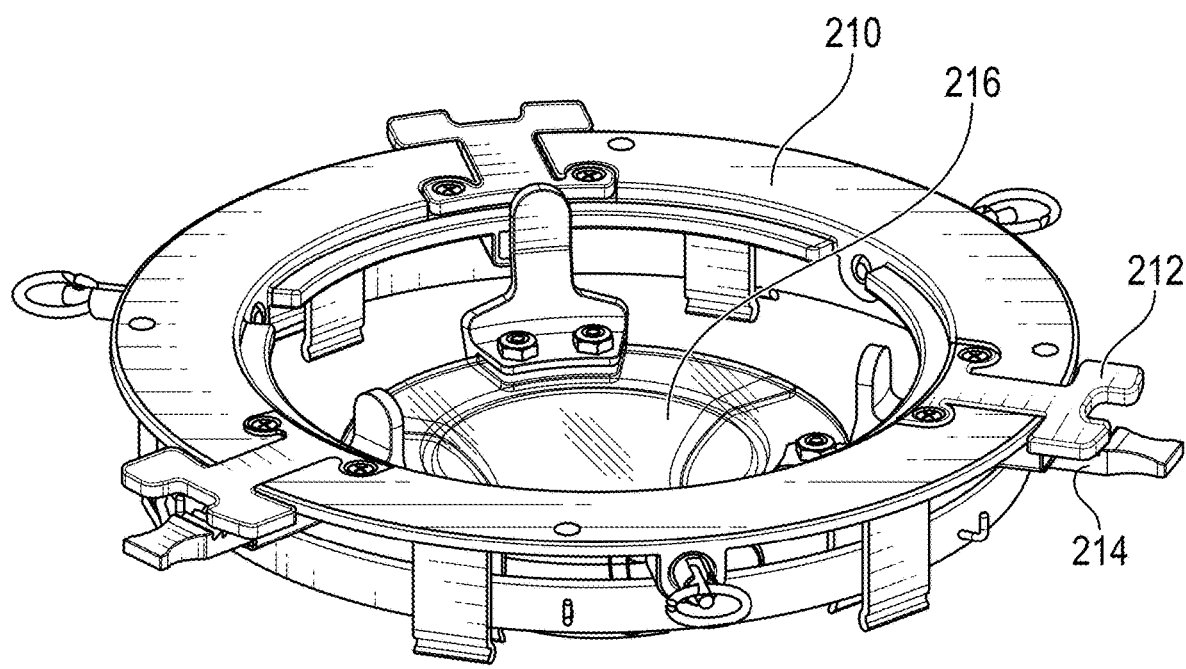
FIG. 26 is a view of a retractor ring that can be coupled to the rolling ring and bag in accordance with the present disclosure.
Figure 27:
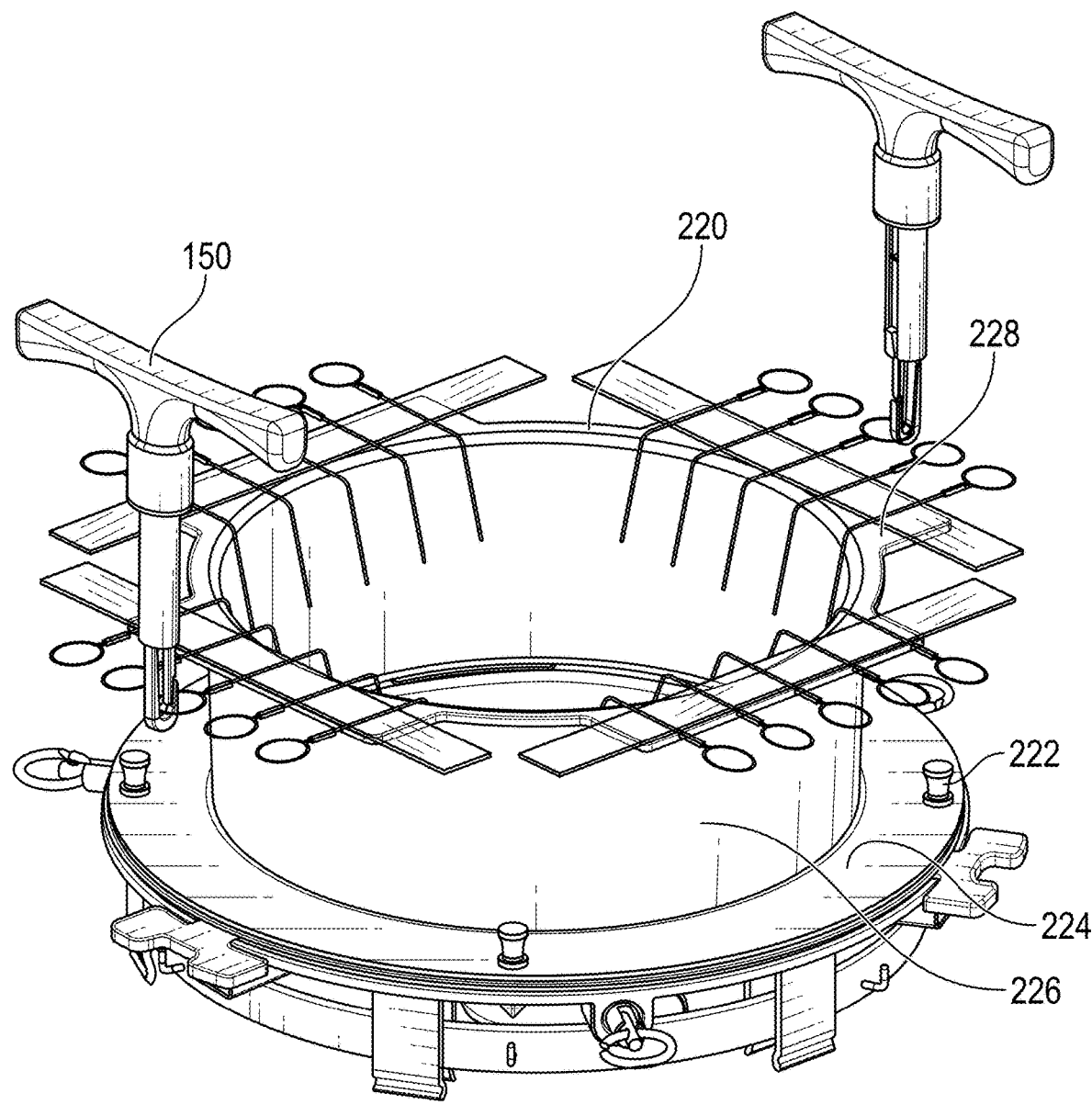
FIG. 27 is an isometric view illustrating the retractor ring of FIG. 27 with a removable sleeve coupled thereto that performs a function similar to the frame of the disclosure.
Figure 28:
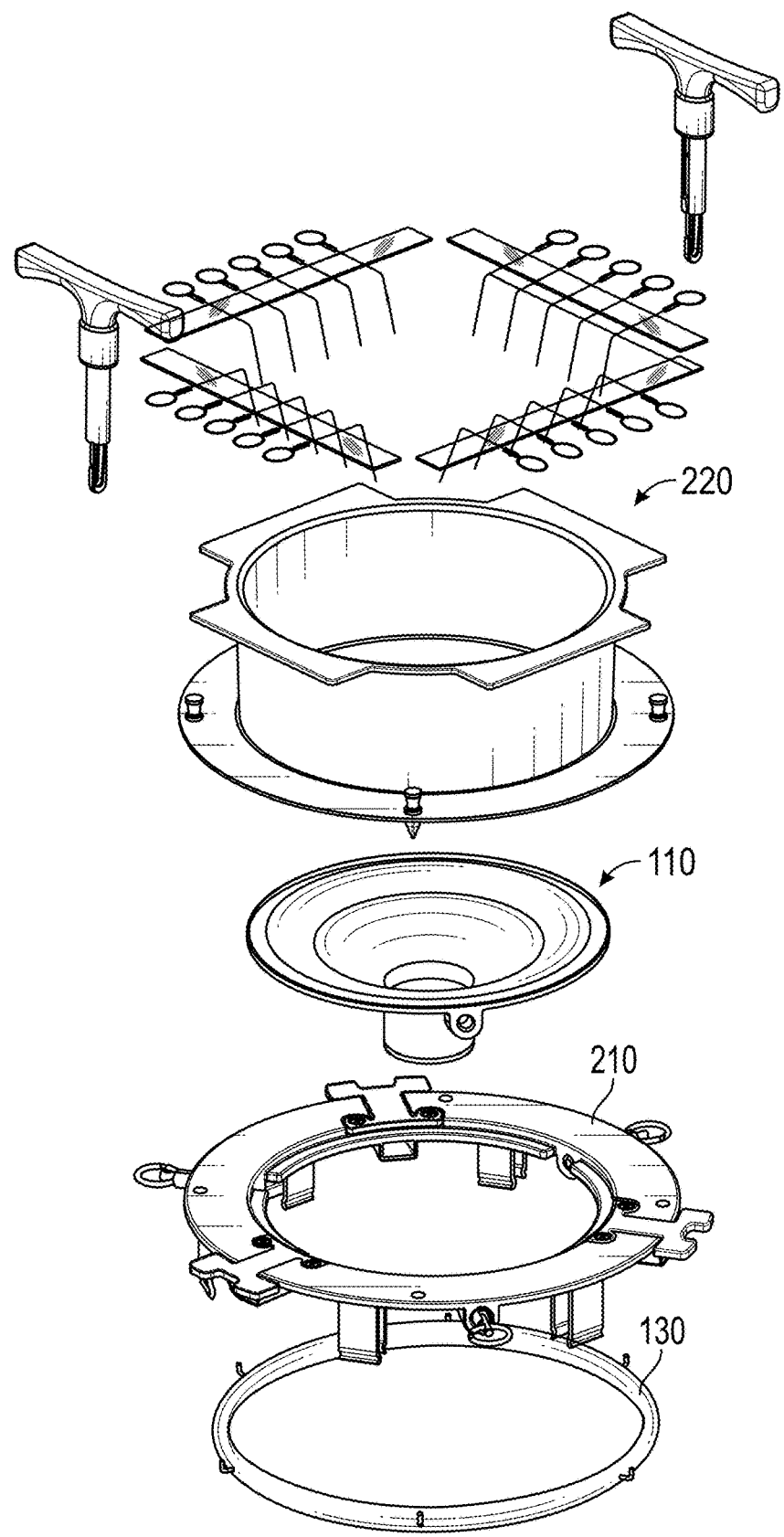
FIG. 28 is an isometric exploded view of the assembly of FIG. 27.
Figure 29:
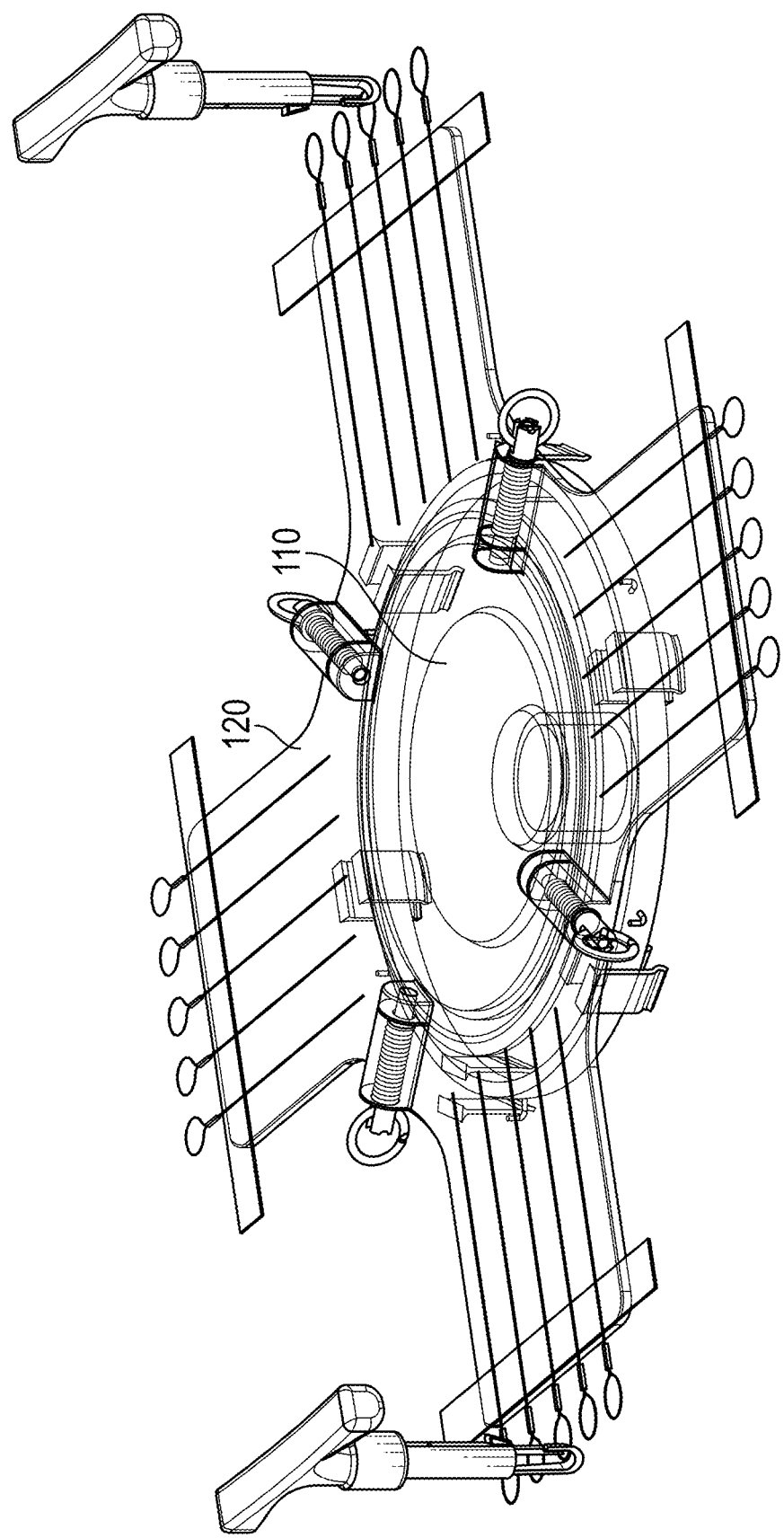
FIG. 29 is a schematic transparent isometric view of the frame and wound protector disc showing relative placement of components.

FIGS. 26-27 show isometric views of a further embodiment of a tissue extraction device 100 including a retractor ring 210. Retractor ring 210 includes at least one retractor detent 212. Retractor detent 212 includes a ratcheting pawl retractor connection. The rack of the ratchet is on retractor arm 214. Retractor detent 212 is coupled to frame 210. When retractor arm 214 is position within a channel, a pawl interfaces with a rack on the retractor arm 214. FIG. 28 shows an exploded isometric view of the assembly of FIG. 27. FIG. 29 shows a wireframe view of the frame 120, disc 110 and cutters 170.

The following is an example method of use of system 100. An incision (e.g., 2.5 centimeters (cm) long) is created in a patient's skin with a knife (e.g., scalpel). A cannula, for example, one having a 2.8 cm diameter, is inserted through the incision using a metal and/or plastic trocar (e.g., a taper point or cutting/trocar point). The inner diameter of the cannula should be at least the length of the incision (e.g., 2.5 cm). The trocar is then removed, but the cannula is left in place.

A bag, such as bag 140 contains a plurality of molded, flexible tracks/guides for a plurality of cutters 170. Each cutter 170 preferably has a color-coded and/or numbered handle coupled to each end of the cutters. For example, if there are four cutting elements then there are eight color-coded and numbered handles.

The upper portions of the cutters strands are held in place against the sides of the bag (e.g., with plastic tabs) so that they do not become tangled when the bag is rolled or compressed. The plastic tabs can be perforated so as to facilitate freeing the cutting elements or strands from the bag. The handles can be staggered in height so as to facilitate passing the bag through the cannula.

The bag is inserted (pushed) into the patient's body (e.g., the patient's abdomen) through the cannula using an inserter with the bag rolled up (like an umbrella) inside the inserter. The cannula can include a seal that can be used as visual port, for example, for a camera. A camera can facilitate inserting a tissue specimen into the bag. Once the bag is inserted into the patient, the bag lies free. The tissue specimen is then inserted into the bag.

After inserting the tissue specimen in the bag, the neck of the bag is grasped (e.g., with a grasper) and pulled up through the incision. The cannula is then removed. Small tags can be fastened to the edge of the bag to facilitate this process. The ring handles and cutting elements and/or strands are pulled away/detached from the sides of the bag. The bag is attached to bag rolling ring 130 via hooks 132 and rolled taut. Rolling the bag with bag rolling ring 130 may require four hands. To facilitate rolling the bag can be brought up taut against the underside of the incision (e.g., against the abdominal wall). Once the bag is rolled taut such that the tissue specimen is held against the underside of the incision, the cutting elements and/or strands are brought up through the annulus of bag rolling ring 130. Frame 120 is coupled to (e.g., snapped onto) bag rolling ring 130 with the end of bag 140 rolled around it, holding the bag 140 in place.

The cutters 170 can be removably attached to the disc 110 and/or the frame 120 as illustrated herein.

The cutters 170 can be individually removed from the inner surface of the bag 140 and any retainer clips, one at a time, and pulled back and forth in a sawing motion. The cutters quickly reduce the tissue specimen to smaller, manageable sized pieces. When one of the cutters and/or strands cuts all the way through the tissue specimen, that cutting element or strand is removed. The cutters 170 are utilized and removed sequentially according the numbers assigned to each of the handles. After all of the cutting elements and/or strands have cut through the tissue specimen and have been removed from inner disc 110 through the opening of disc 110, disc 110 is separated and/or removed from frame 120.

As illustrated retractor ring 210 includes three retractor detents 212, each located at the ten o'clock, two o'clock, and six o'clock positions. Retractor arms 214 of three retractors are then positioned into channels of retractor ring 210. Retractors include retractor blades 216 coupled to retractor arm 214. Retractor arm 214 includes a knurled shaft including a rack that interfaces with a pawl of retractor detent 212 to form a ratchet. The ratchet allows retractor arm 214 to be tightened (pulled away from the center of the incision) and held in place. Retractor blades 216 can each be a curved piece of semi-rigid, semi-flexible plastic. Retractor blades 216 can be inserted into the incision. As illustrated, each one of the three retractor blades 216 can overlap with the adjacent two retractor blades 216, so as to form a collar that completely lines and protects the inside of the incision.

The cut pieces of the tissue specimen are extracted through the collar of retractor blades 216 that protect the neck of the bag. If a cut piece of the tissue specimen is too large to fit through the collar, the cut piece can be cut again using a knife (e.g., scalpel). After the cut pieces have been extracted from the bag, the bag is removed along with frame 120 and retractor arms 214. If the bag is a dual layer bag, the space between the inner and outer layers, if inflated with insufflation gas, can be deflated and removed along with the bag 140.

Figure 30:
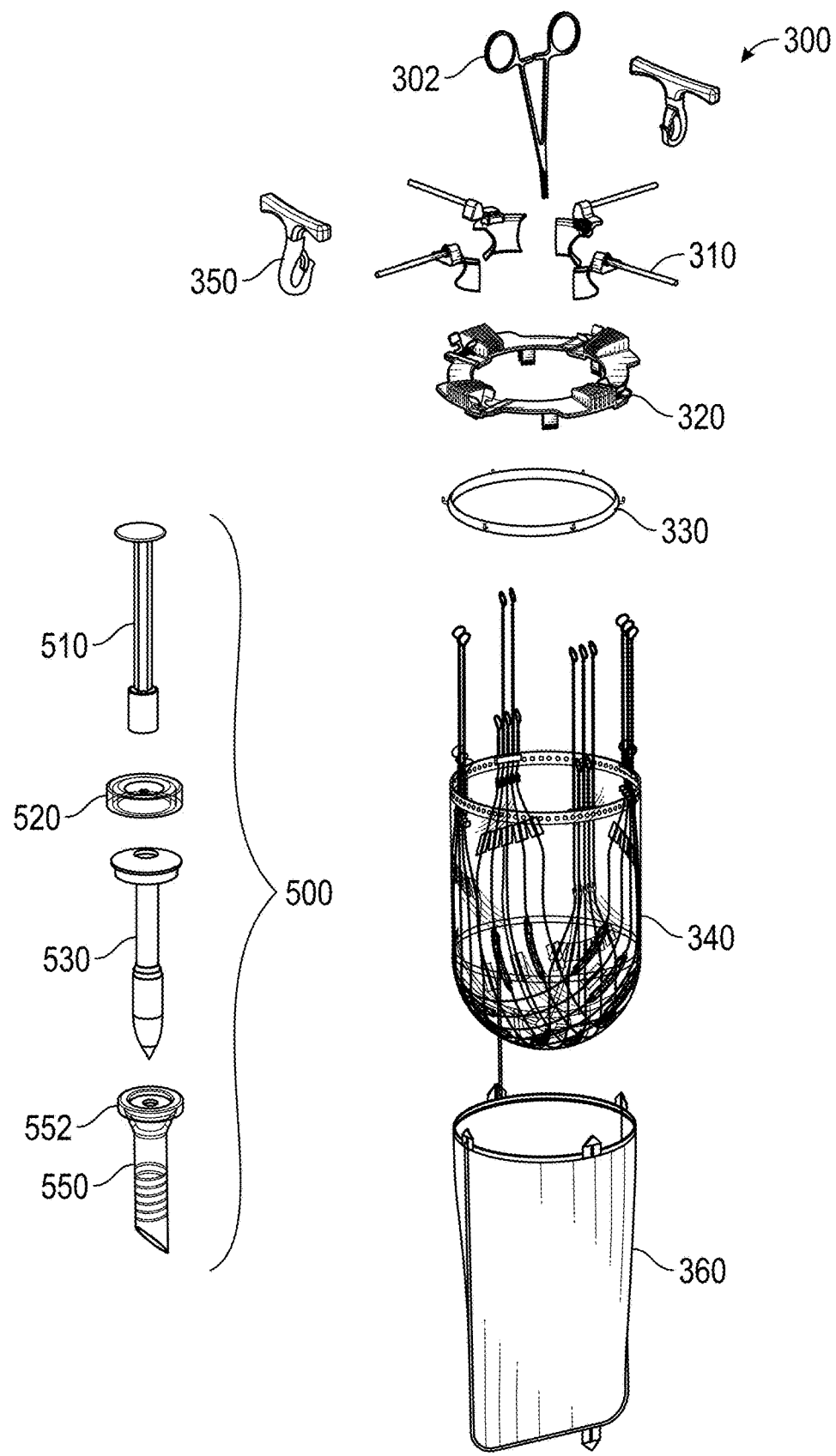
FIG. 30 is an exploded view of a further embodiment of a tissue extraction system in accordance with the present disclosure.

For purposes of illustration, and not limitation, a further embodiment of a tissue extraction system 300 is illustrated in FIG. 30 in an exploded view. FIG. 30 illustrates sub components of the system 300, including an inner bag 340 to receive a tissue sample to be dissected and a pair of graspers 302 to remove cut tissue. Inner bag 340, is in turn configured to be coupled to a rolling ring 330. The ring 330 is configured to be received by an underside of platform, frame or ring 320. Platform 320 is configured to removably receive retractors 310 by way of one or more fasteners 307 or clips that are mounted on frame 320. Bag 340 includes a plurality of cutters 343 configured to be coupled to gripping handle hooks 350. An outer bag 360 can be provided to capture any fluids or tissues not contained by bag 340 during the tissue dissection and removal process.

As mentioned above, system 300 includes a bag rolling ring 330, similar to the earlier embodiment 100. Bag rolling ring 330 is removably coupled to platform 320 via at least one fastener. Bag rolling ring 330 can include at least one hook 332 to which the bag 340 can be coupled. For example, bag rolling ring 330 can include pins, posts, bosses, and/or clips to couple bag 340 or a different bag to bag rolling ring 330. Bag rolling ring 330 is used to roll the bag 340 around bag rolling ring 330. Bag rolling ring 330 is made from a material with a firmness sufficient to prevent buckling during rolling the bag and to maintain optimal tension on a tissue specimen inside the bag.

FIG. 30 further illustrates an introducer assembly 500 to introduce the inner and outer bags 340, 360 into a patient. The introducer assembly 500 includes a cannula 550 to be introduced into a patient in cooperation with a trocar 530 received therein and a cap 520 to cover the cannula 550 after it is inserted. Introducer assembly 500 is discussed further below with reference to FIGS. 38 and 39.

Figure 31:
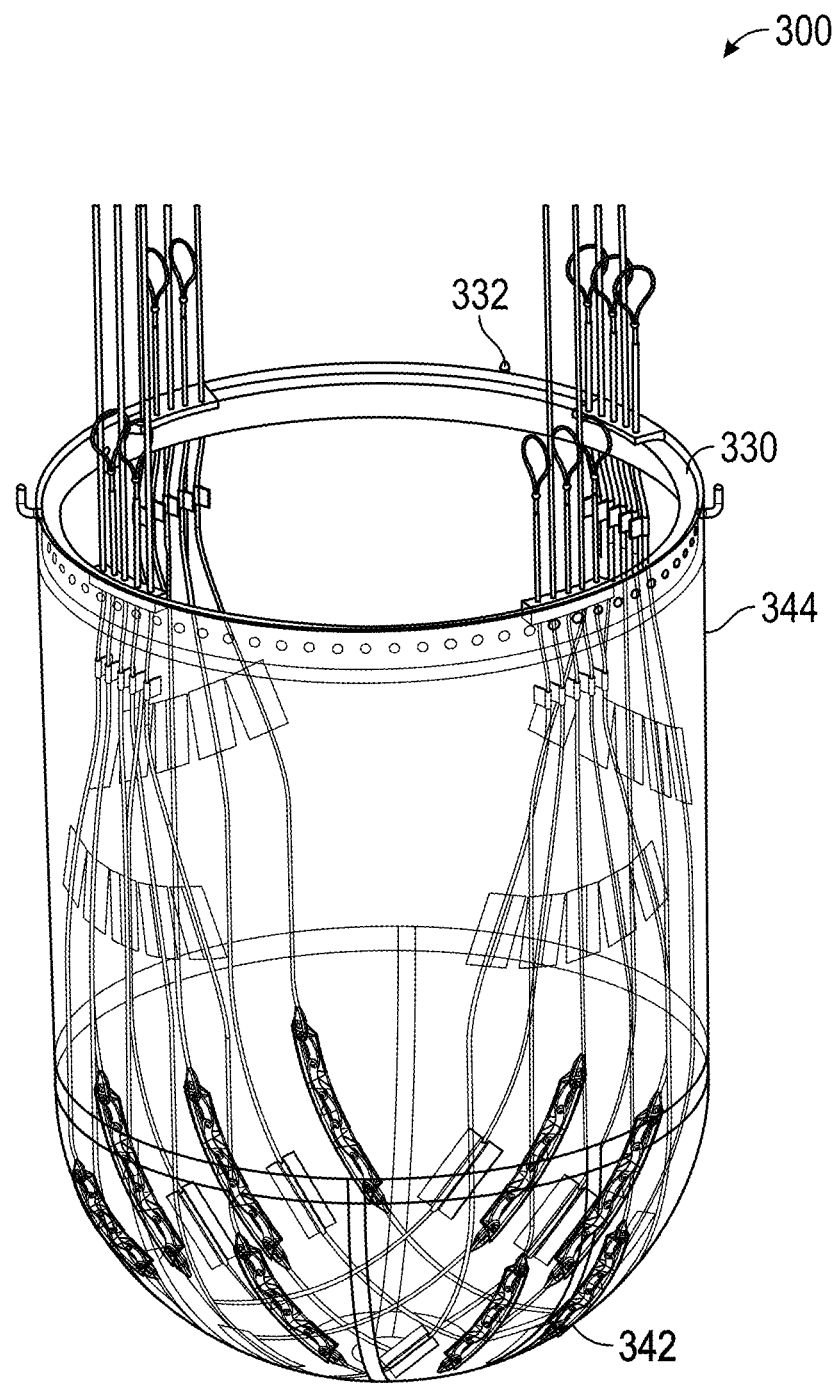
FIG. 31 is an isometric view of an inner bag in accordance with the disclosure.
Figure 32:
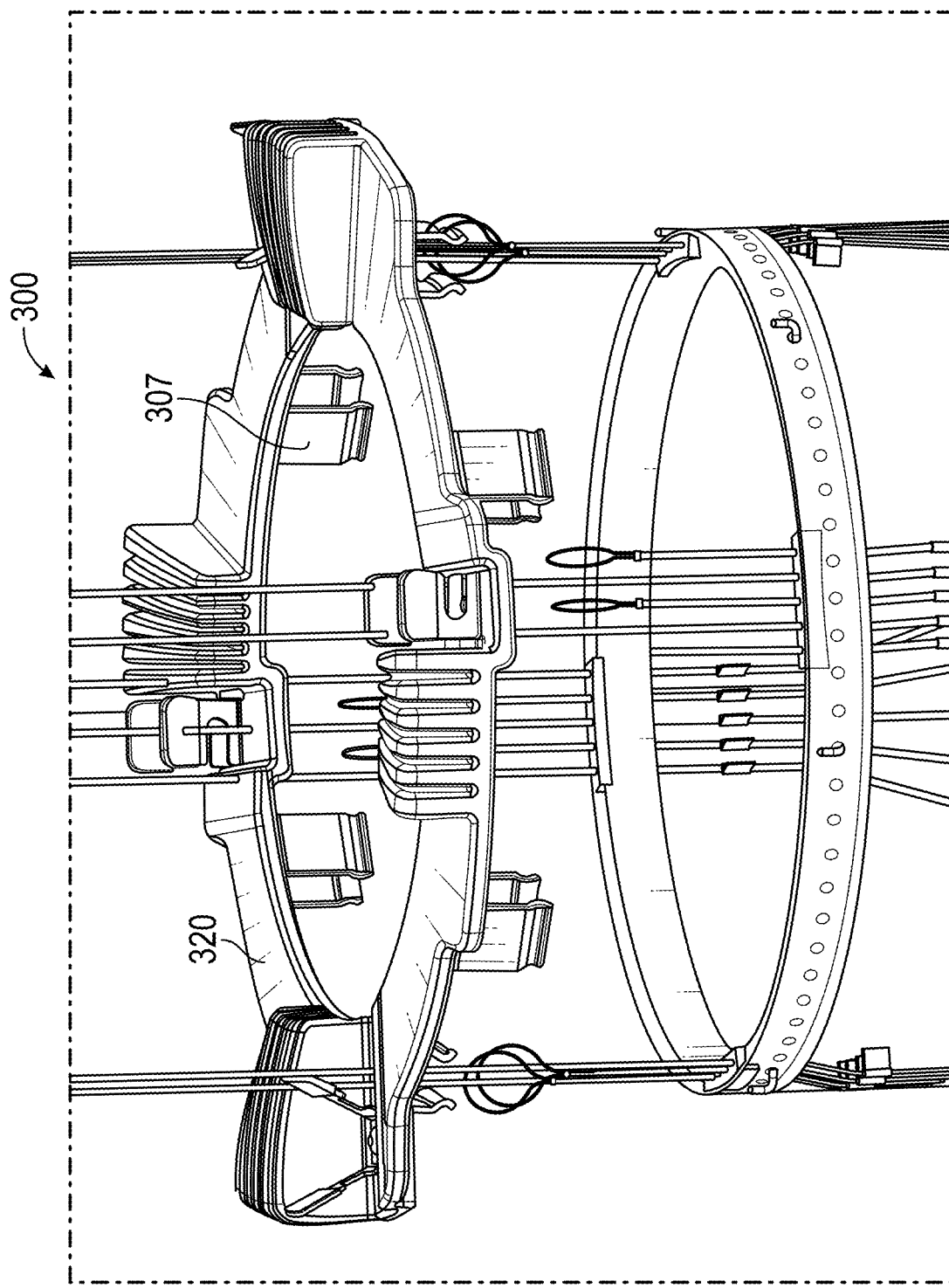
FIG. 32 is an isometric view of the inner bag of FIG. 31 showing relative orientation to a platform.

FIG. 31 presents an isometric view of the inner bag 340 coupled to the bag rolling ring 330 by way of hooks 332, similar to the first embodiment of the disclosure. The cutter strands are moved aside and the rolling ring is hooked into the holes disposed bout the periphery of the bag. The bag and ring are then rolled "inwardly" to tighten along the direction of the arrows. FIG. 32 shows relative orientation of the bag 340 to platform 320 prior to rolling the bag 340 about rolling ring 330 and clipping the rolling ring to clips or fasteners 307 (six clips 307 being present in the illustrated embodiment) disposed on the underside of the platform 320, wherein the illustrated clips 307 each include a first arm and second arm that bend away from each other as the rolling ring with the bag rolled around it are pushed into the arms. The arms then spay apart and snap over the combined rolling ring and bag. As illustrated, bag 340 includes a sidewall 344 that is coupled to a bottom portion 342 that cooperate to surround a volume.

Figure 33:
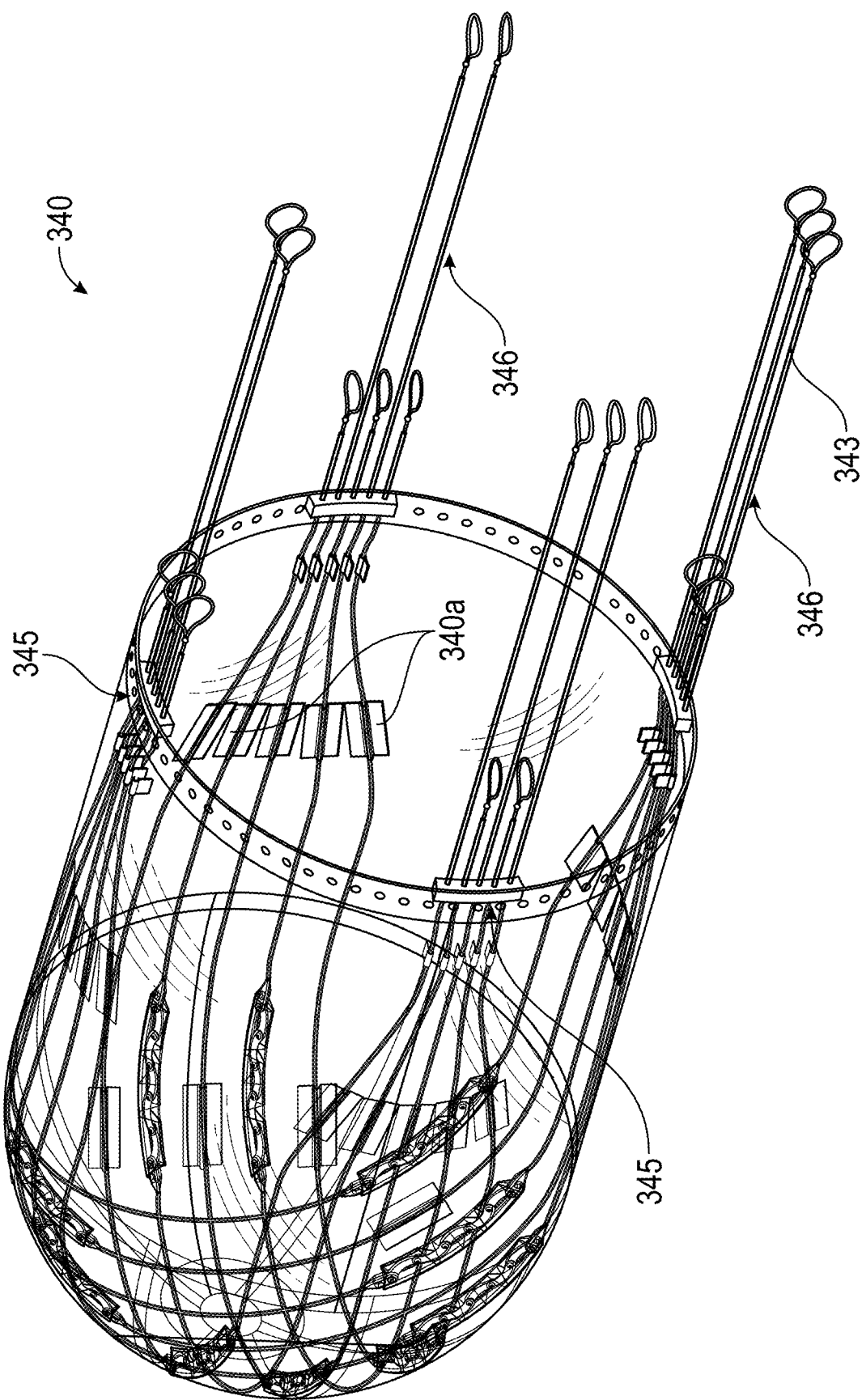
FIG. 33 is a further isometric view of the inner bag of FIG. 31.

As illustrated in FIG. 33, bag 340 defines a generally cylindrical volume with a hemisphere at a bottom closed end thereof. Cutters 343 are disposed about the bag 340 in a manner similar to embodiment 100 above. However, while the cutters of the embodiment in FIG. 4 extend along a straight direction that is parallel to a central longitudinal axis of the bag, it is illustrated, particularly in FIGS. 31 and 33, that each grouping of a plurality of (e.g., five) cutters 343 actually converges together along the length of the sidewall of the bag as the cutters approach the open peripheral edge of the bag. The cutters converge toward and pass through openings defined through blocks 345 that are coupled to an inner surface of the bag 340. As illustrated, the blocks 345, which can be made of foam, for example, are flexible, and can be attached at or near the open peripheral top of the bag 340. The blocks 345 that manage the strands are removable by tearing apart or pulling off ends of cutters once strands are dressed into the frame. Arranging the cutters 343 in this manner results in it being easier to collapse the bag 340 to facilitate introduction of the bag 340 into the patient.

Figure 34:
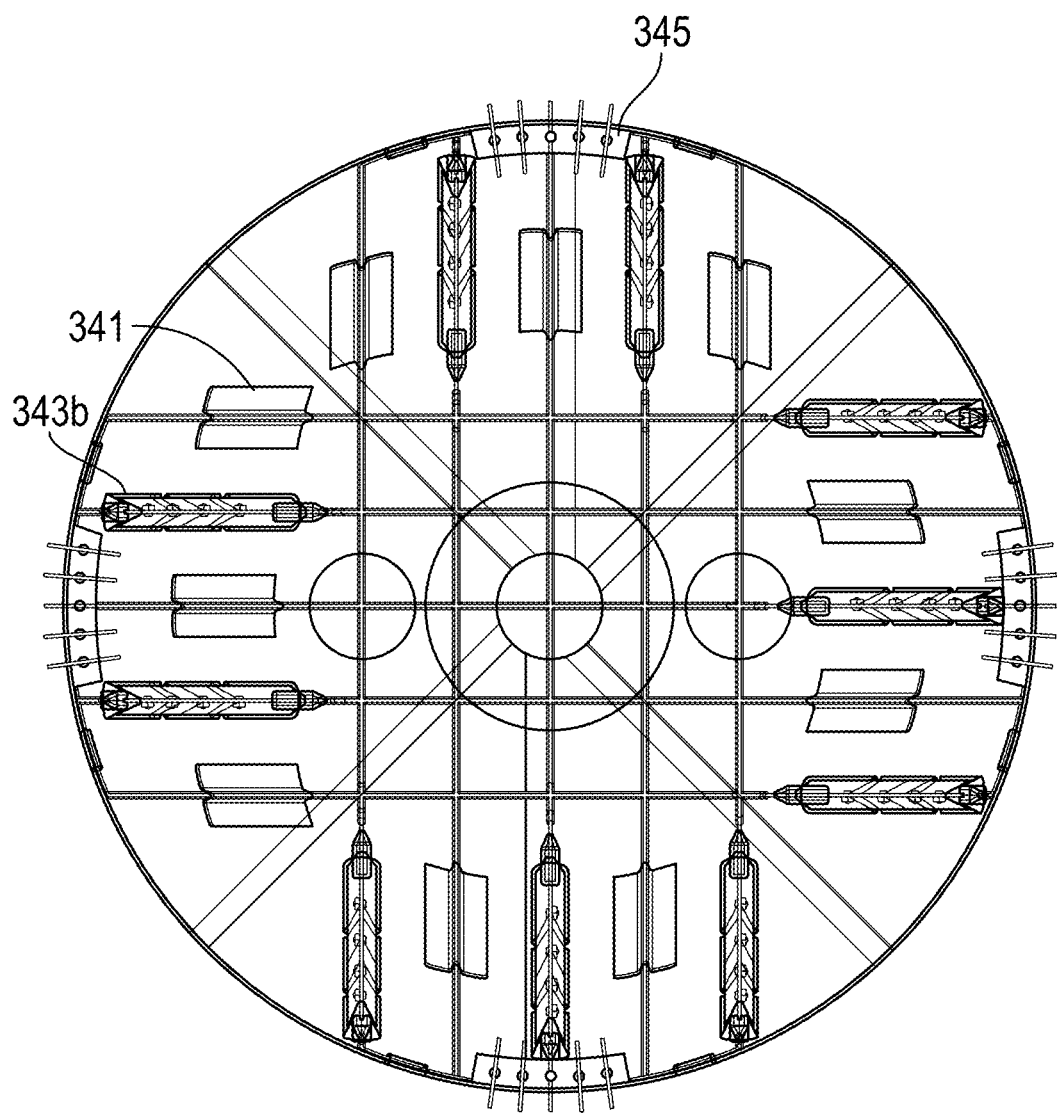
FIG. 34 is a top view of the inner bag of FIG. 31.

With reference to FIGS. 33 and 34, each cutter 343 is held in place against the inner surface of the bag 340 by a piece of tape 341, as well as a block 345 on either side of the bag 340. Each strand portion of each cutter 343 is surrounded by a piece of tubing 346 that protects the strands during cutting, keeps them organized, and aligned and prevents them from crossing or getting caught on or tangled with other system components. Each cutter 343 also traverses underneath a further tape, or layer of film 340a that is attached to the inner surface of the bag 340. FIG. 34 sets forth a top view of bag 340 looking down, inside the bag 340.

With reference to FIGS. 34 and 35, each cutter 343 includes a cutting region or blade assembly 343b attached at either end to a tether or strand 343a that terminates in a loop 343h. Polymeric tubing 346 can be provided to surround the tether or strand 343a as well as to help define the loop 343h. The tubing can be coextensive with the tether length to prevent binding, and also to help improve sliding between the cutter assembly 343 and the tissue it is siding through as well as other surfaces of the system 300. Each loop 343h can be defined by knotting the tether 343 a at a knot 343f. Each section of tether 343a can be provided in a different color to act as visual indicia, or be provided with other indicia. While color has not been reproduced in the drawings as filed, one can visualize one section of the tether 343a being "yellow" as indicated, and the other section of tether attaching to the other end of the cutter being "green." As illustrated, each of the "yellow" and "green" tethers attaching to either end of the blade assembly 343b are of equal or approximately equal length. But, as illustrated, the cutters are not mounted symmetrically in the bag. Specifically, while the midpoint of the overall cutter length 343 is illustrated as being in the middle of the blade assembly 343*b*, the blade assembly itself 343*b* is not mounted at the bottom of the bag, but offset on the sidewall of the bag. Thus, as illustrated in FIG. 34, each blade assembly 343*b* is mounted along the curved dome portion 342 of the bag 340. This offset arrangement of the blade assemblies 343*b* distributes the cutting blades evenly around the bag. This facilitates collapsing of the bag to make it easier to introduce into a patient. This arrangement also helps facilitate even grasping of the specimen during cutting. As a consequence of this placement of blade assemblies 343*b*, the ends of each tether section 343*a* extend out of the bag at different lengths. In use, the "shorter" tether is pulled "first" for a given cutter 343 to permit the blade assembly to cut through the tissue during a first cutting stroke. The other end of the cutter is then pulled, and so on, to create a reciprocating sawing motion to advance the blade assembly through the tissue being cut. It will be appreciated that, while five cutters 343 are presented along two orthogonal directions (e.g., 10 cutters total), more or fewer cutters can be provided, depending on the size of the bag and of the tissue sample. The tethers themselves can include fishing line, DACRON® fiber, sutures or wire, as desired. The tethers themselves, or the tubing surrounding the tethers can be color coded.

Figure 36A:
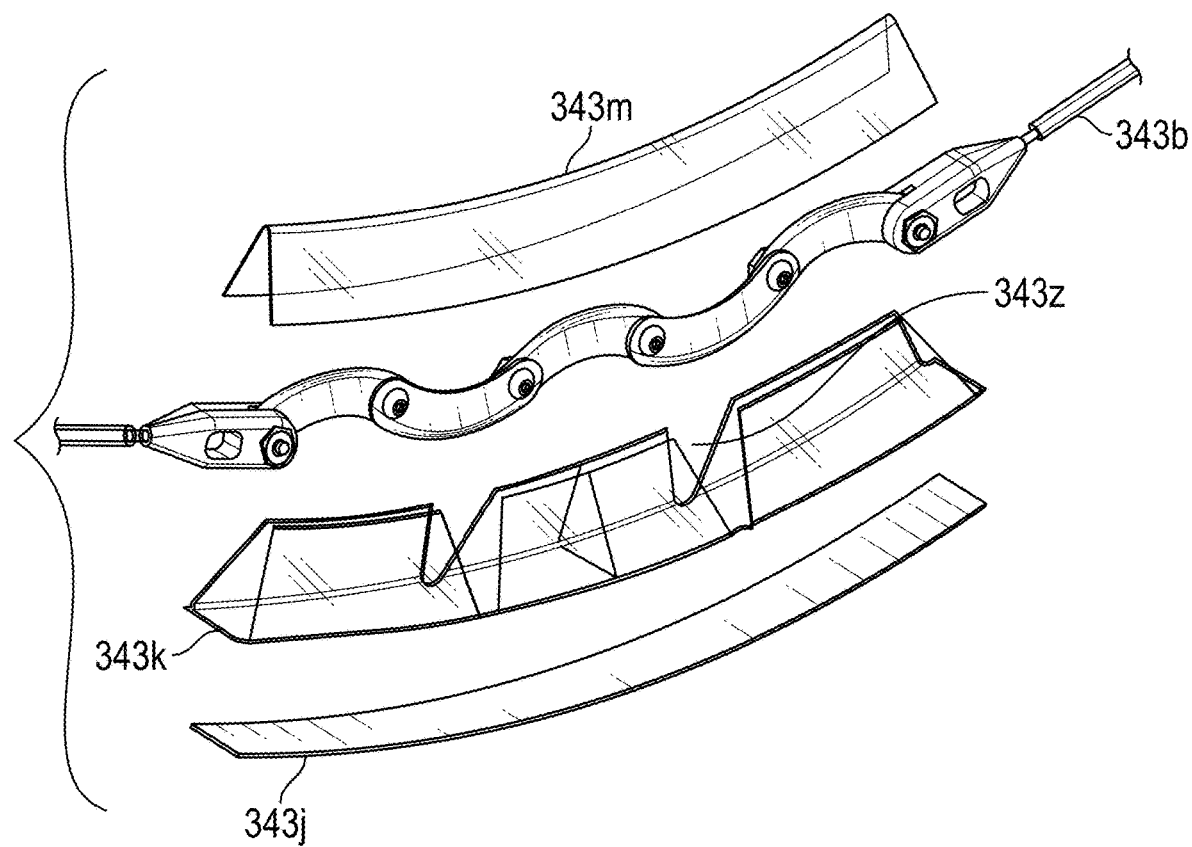
Figure 36B:
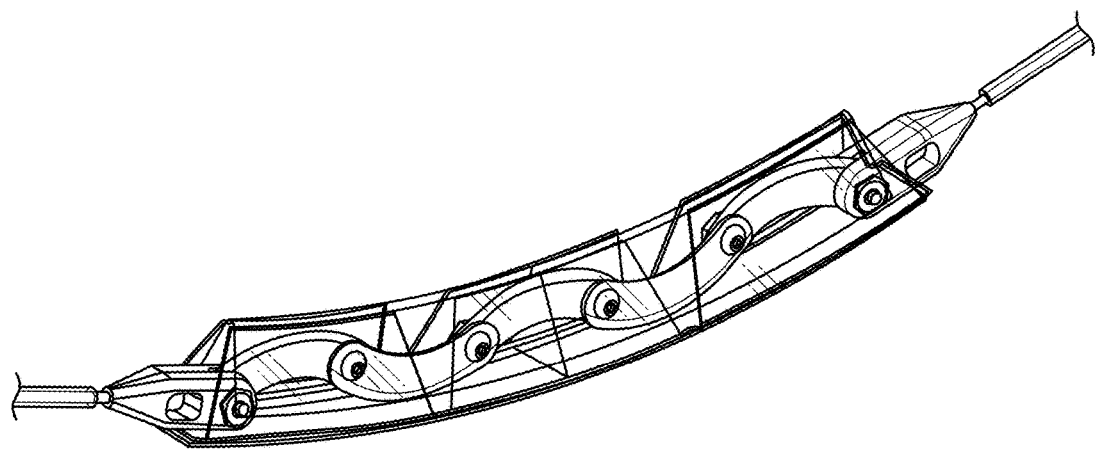
Figure 36C:
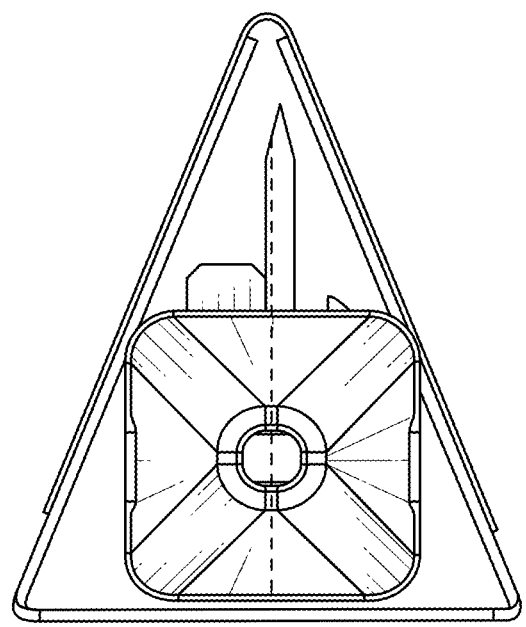

FIGS. 36-37 illustrate aspects of the blade assemblies 343*b* and how they are held in place in the bag 340 prior to use. As can be seen in FIGS. 36A-36C, the overall assembly 343*b* is held to the inner wall of the bag 340 by a retainer assembly. This retainer assembly can include double sided tape or other adhesive 343*j*. The adhesive can connect directly to the blade assembly 343*b*. Preferably though, as illustrated, the tape 343*j* can couple to a blade holder 343*k*. The blade holder includes a backing plate that attaches to the adhesive 343*j* to hold it against the wall of the bag 340, and a plurality of converging side walls that approach each other at a free edge that extends away from the inner wall of the bag. Also, as illustrated, each holder 343*k* can have a plurality of segments to permit the holder 343*k* to match the curvature of the wall of the dome portion 342 of the bag 340. The blade holder 343*k* can have tooth shaped features 343*z* to permit the blade holder to dig into or engage the tissue specimen and prevent the specimen from rolling around during cutting. The converging walls of the holder 343*k* define a space having a triangular cross section (FIG. 36C) to receive the blades. As illustrated, the converging walls urge against upper corner surfaces of couplers of the blade assembly to hold the blade back from exiting the holder. If desired a further adhesive tape 343*m* can be used to hold the converging walls together. As will be appreciated, when used, the user places tension on the tethers that attach to the blade assembly 343*b*. This forces the cutting edges of the blades toward the tape 343*m*, severing the tape, and permitting the blade assembly 343*b* to be pulled out of the holder 343*k*. FIG. 36A presents an exploded view of the assembly, FIG. 36B presents the assembly prior to use, and FIG. 36C presents an end view of the assembly.

As illustrated in FIGS. 37A-37C, each blade assembly 343*b* includes a plurality of links or blades 343*n* that is arcuately shaped with a pair of cutting edges, wherein one of the edges is convex, and the other concave. Each blade 343*n* defines an opening through either end to permit each end of the blade 343*n* to be coupled to an adjacent blade or a blade end adapter 343*p* by way of a pin, rivet or screw and nut 343*q*. As illustrated, the curvature of each subsequent blade is alternated so that the overall cutting edge formed by the blades is serpentine in shape to maximize the chances of tissue contact to facilitate cutting. Each blade end adapter 343*p* includes a body having a first end that defines a groove therethrough to receive an end of a blade 343*n* and defines a bore transversely across the groove to pivotally receive the blade 343*n*. The opposing end of the adapter includes a bore to receive a tether 343*a* therein to be connected by crimping, knotting or other suitable means.

Figure 38B:
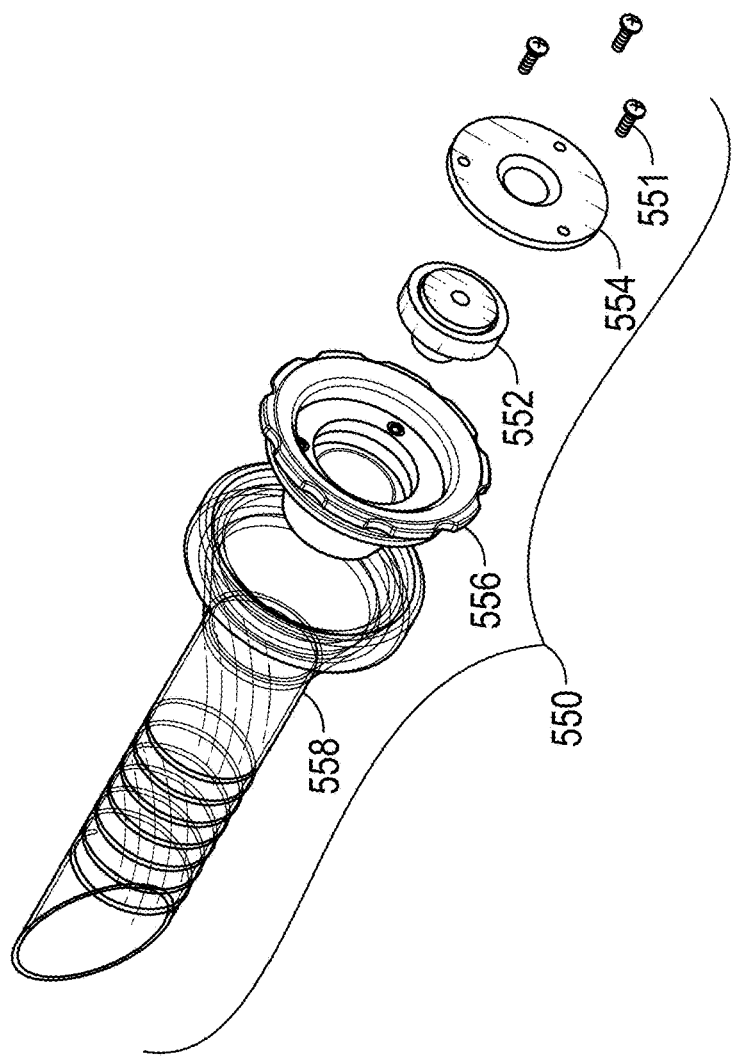
FIGS. 38A-39 illustrate aspects of a cannula assembly in accordance with the present disclosure.
Figure 38A:
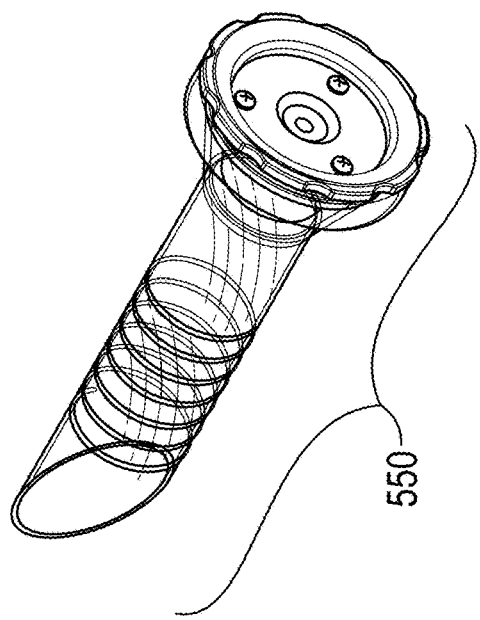
Figure 39:
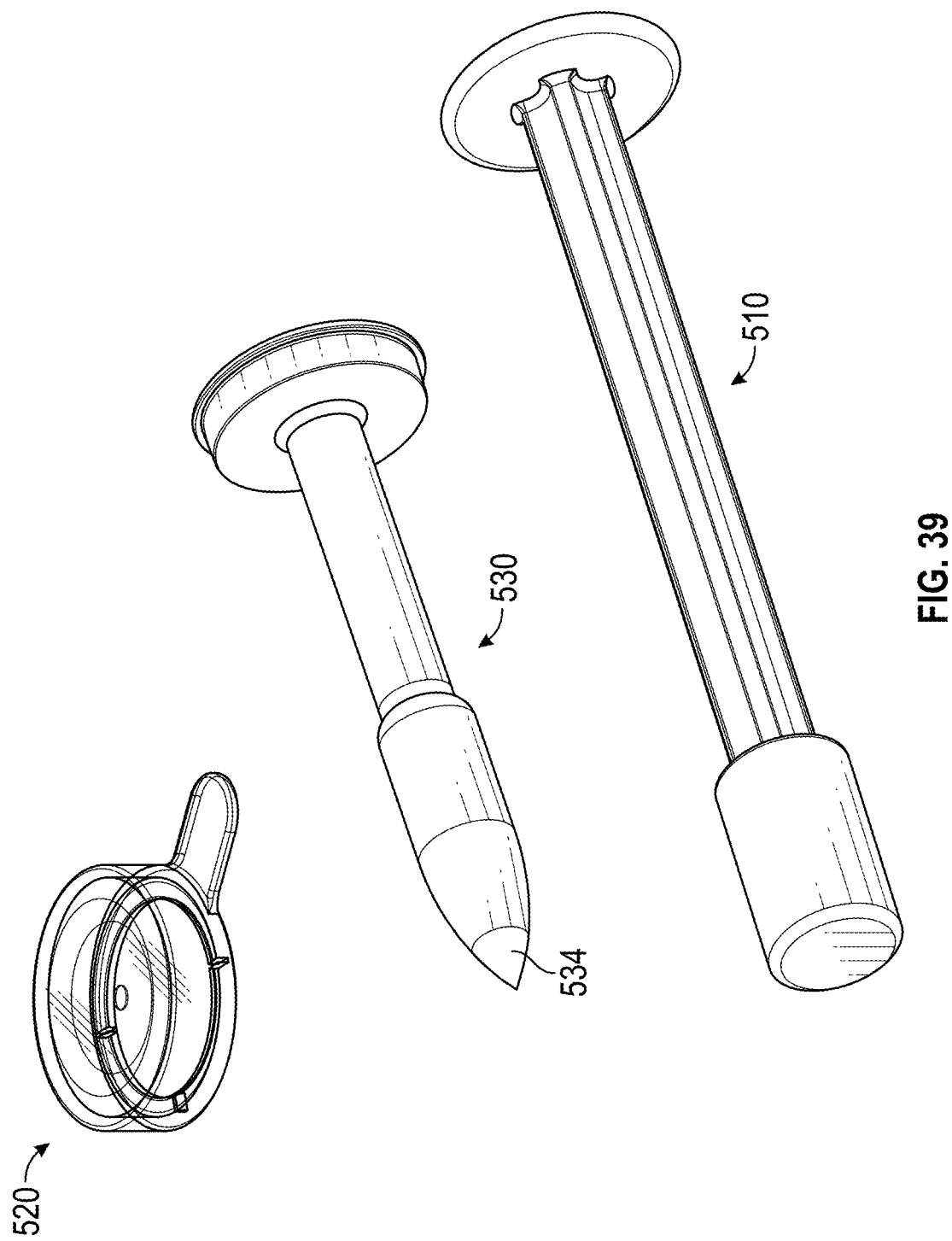

FIG. 38A presents a cannula assembly that is presented in exploded isometric view in FIG. 38B. The cannula includes a proximal end and a distal end and defines a passage therethrough from the proximal to the distal end. The proximal end of the cannula 58 defines a funnel shape to receive a funnel shaped inner housing 556 that defines a central longitudinal passage therethrough. The central passage is configured to receive a minivalve or duck bill valve 552 therein to prevent the outflow of insufflation gas from the patient's peritoneum. An outer housing or 554 is provided to hold the valve 552 in place. The assembly can be welded together, or be joined by adhesive and/or fasteners 551. FIG. 39 sets forth an isometric view of a trocar or obturator 530 having a proximal end ending in a handle and a converging distal tip sufficient to perform sharp or blunt dissection of tissue through abdominal tissue into the peritoneum. The trocar 530 is coupled to the cannula assembly 550 to introduce both instruments into the peritoneum after it is insufflated by way of a Veress type needle. The trocar 530 is removed, leaving the cannula assembly 550 in place. The cap can be placed over the cannula assembly if desired to reduce gas outflow not stopped by the valve 552 and to prevent debris from falling into the cannula assembly 550. Once the trocar is removed, the introducer 510 can be used to push the inner and outer bag assembly into the patient to permit a tissue specimen to be cut into the inner bag 340, and the open ends of the bags 340, 360 can be removed outwardly through the incision in the patient, and the bag 340 can be attached to the rolling ring 330 and rolled to place the tissue specimen under tension and pull it toward the surgeon. The rolling ring 330, with the bag 340 wrapped around it can then be attached to the platform 320.

Figure 40A:
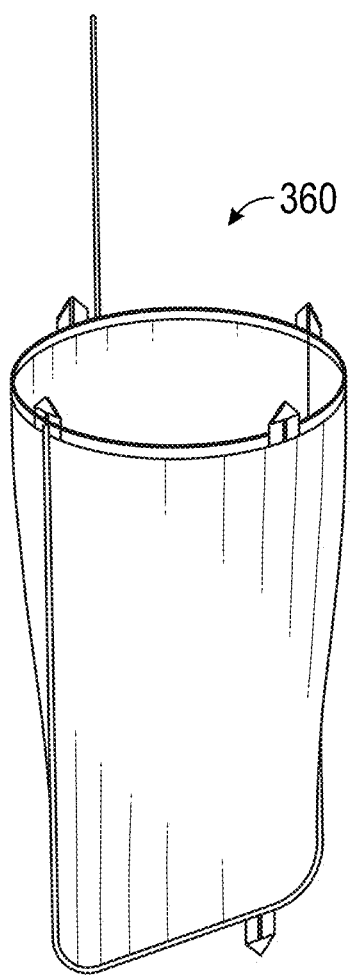
FIGS. 40A-41B illustrate aspects of an outer bag assembly in accordance with the present disclosure.
Figure 40B:
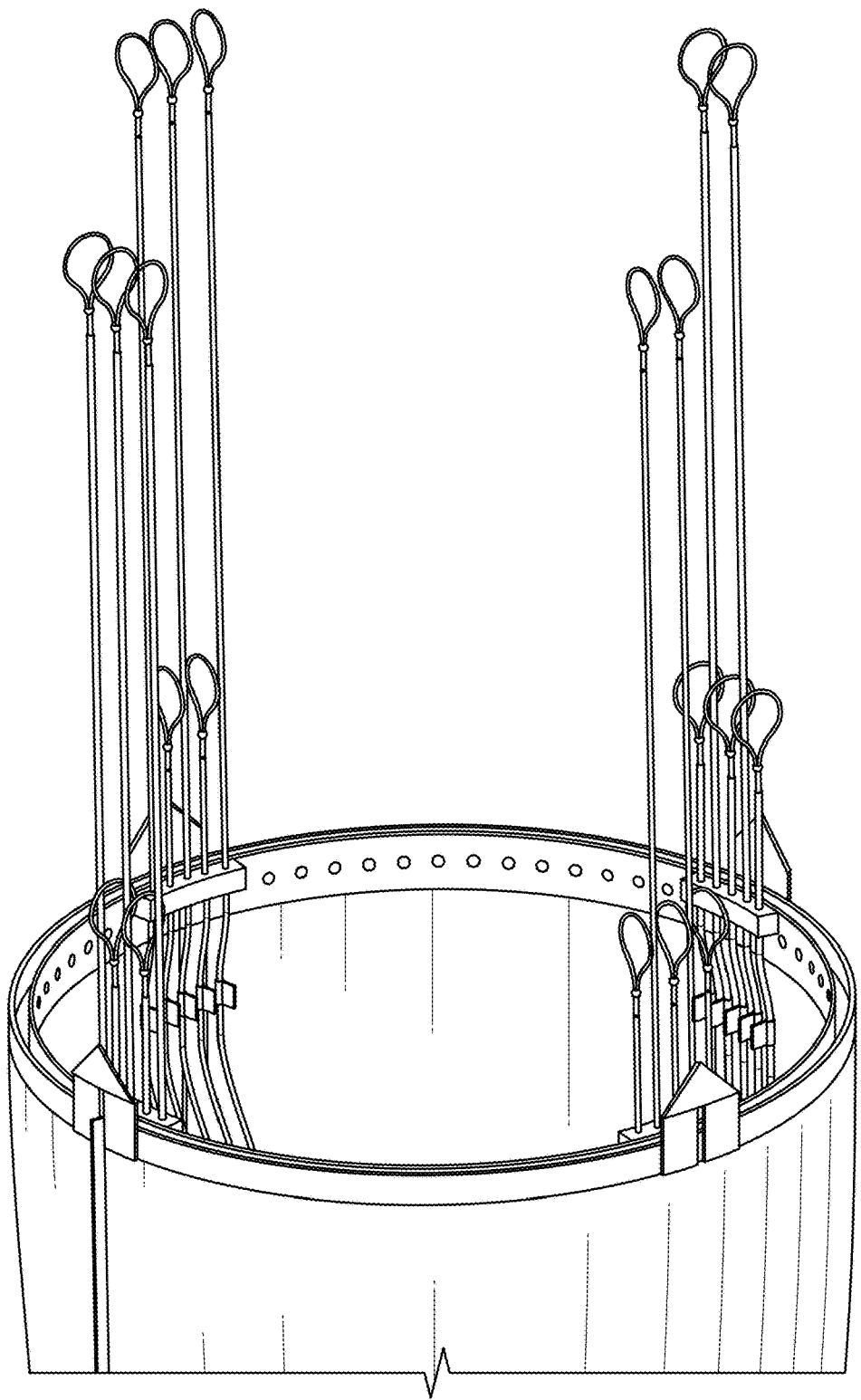
Figure 40C:
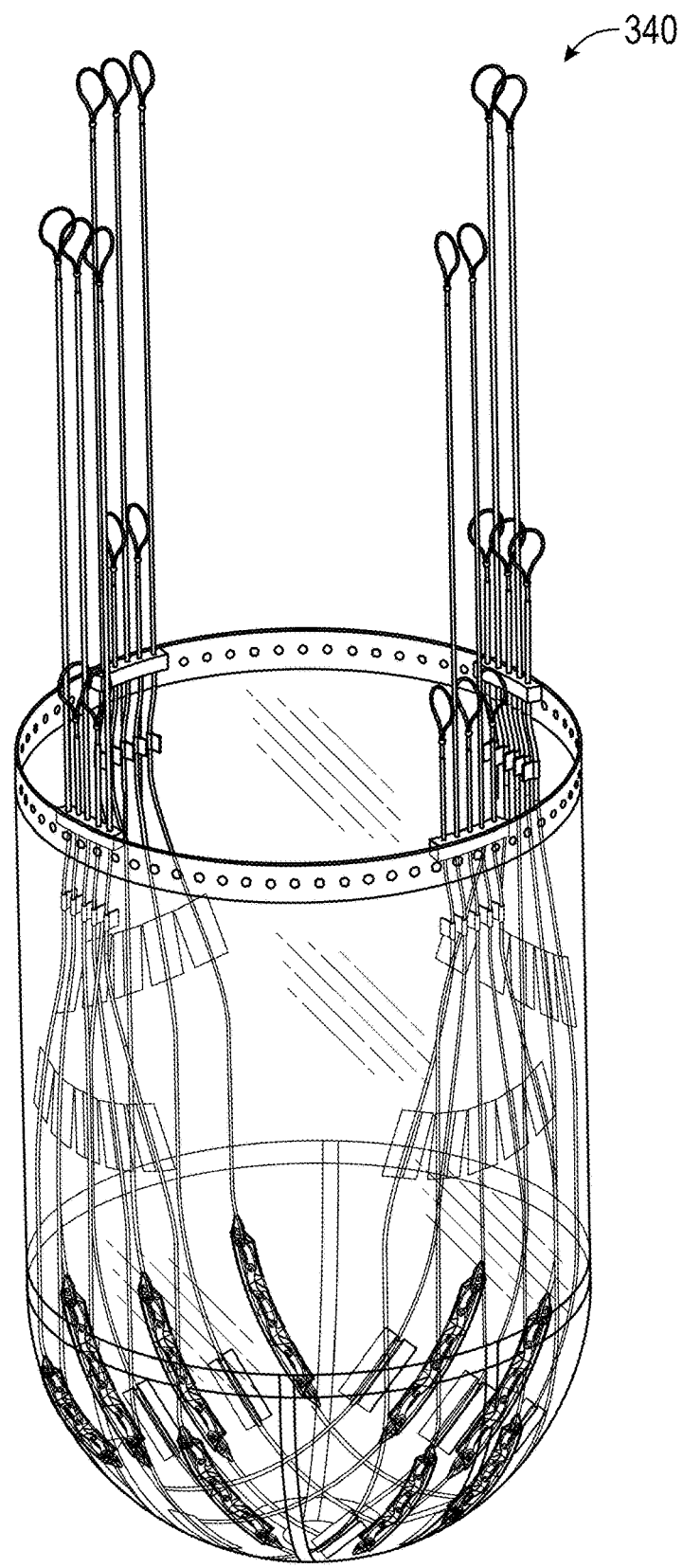
Figure 41A:
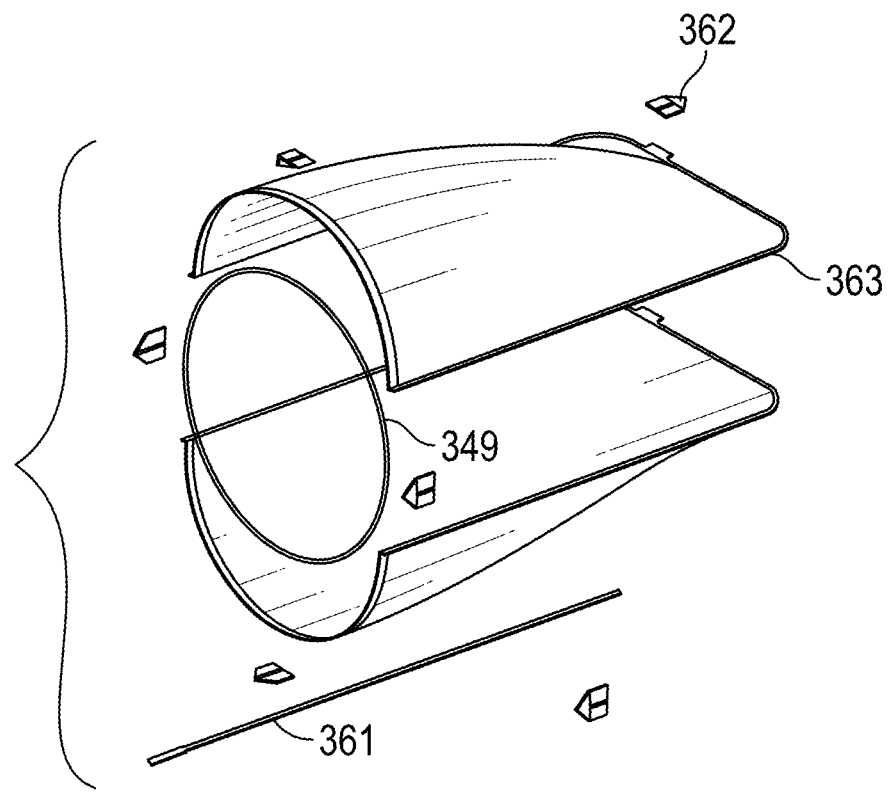
Figure 41B:
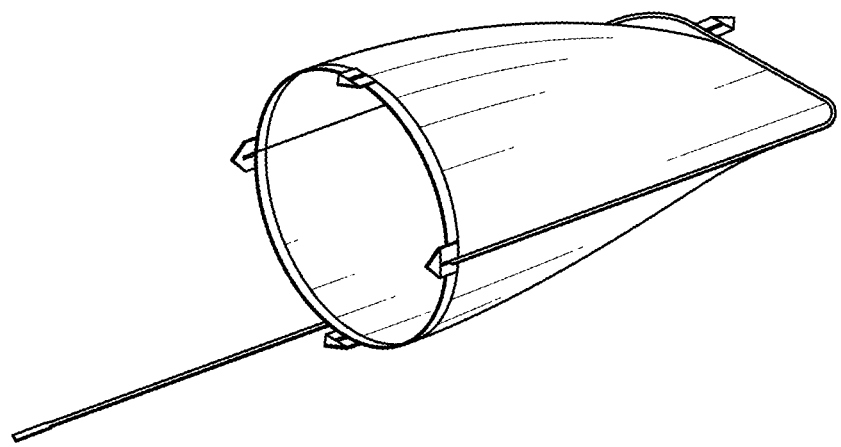

FIGS. 40-41 illustrate certain aspects of the inner bag 340 and outer bag 360. As can be seen, the outer bag 360 surrounds the inner bag 340. The inner bag 340 is inserted using the introducer 510 while it is surrounded by the outer bag 360. The surgeon maneuvers a tissue sample to be cut into the inner bag 340, and uses forceps or other suitable instruments to withdraw the open ends of both bags 340, 360 out of the incision from the peritoneum and externalizes the upper edges of both bags. The upper edge of bag 340, which includes a stiffening ring 349 integrated therewith is permitted to expand to the shape of the ring 349. Ring 349 can be made from shape memory material, such as a NiTi allow (e.g, Nitinol®). Bag 340 can then be mounted on ring 330 and rolled up. As bag 340 shortens from being rolled up, the excess material of bag 360 can also be pulled up using tether 361 and/or tabs 362, where the upper ends of the bag 360 can be spread out into an apron shape for the platform 320 to rest on while the procedure is being performed. As depicted, bag 360 can be made from two shell portions 363 that are joined along their edges. The placement of ring 349 of bag 340 is shown relative to the outer bag 360 in FIG. 41A.

Figure 42A:
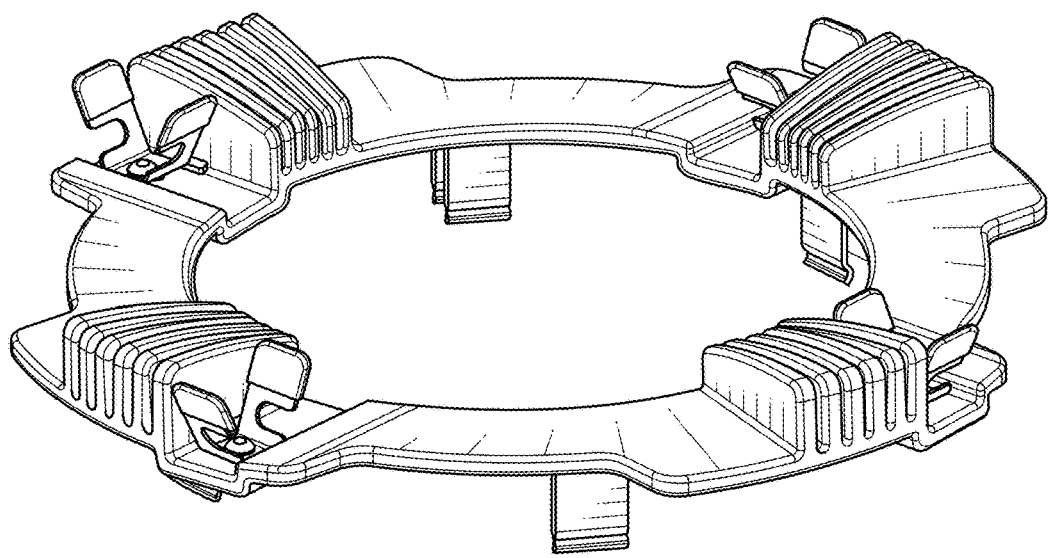
FIGS. 42A-47C illustrate aspects of a platform and relative placement of retractors and cutters in accordance with the present disclosure.
Figure 42B:
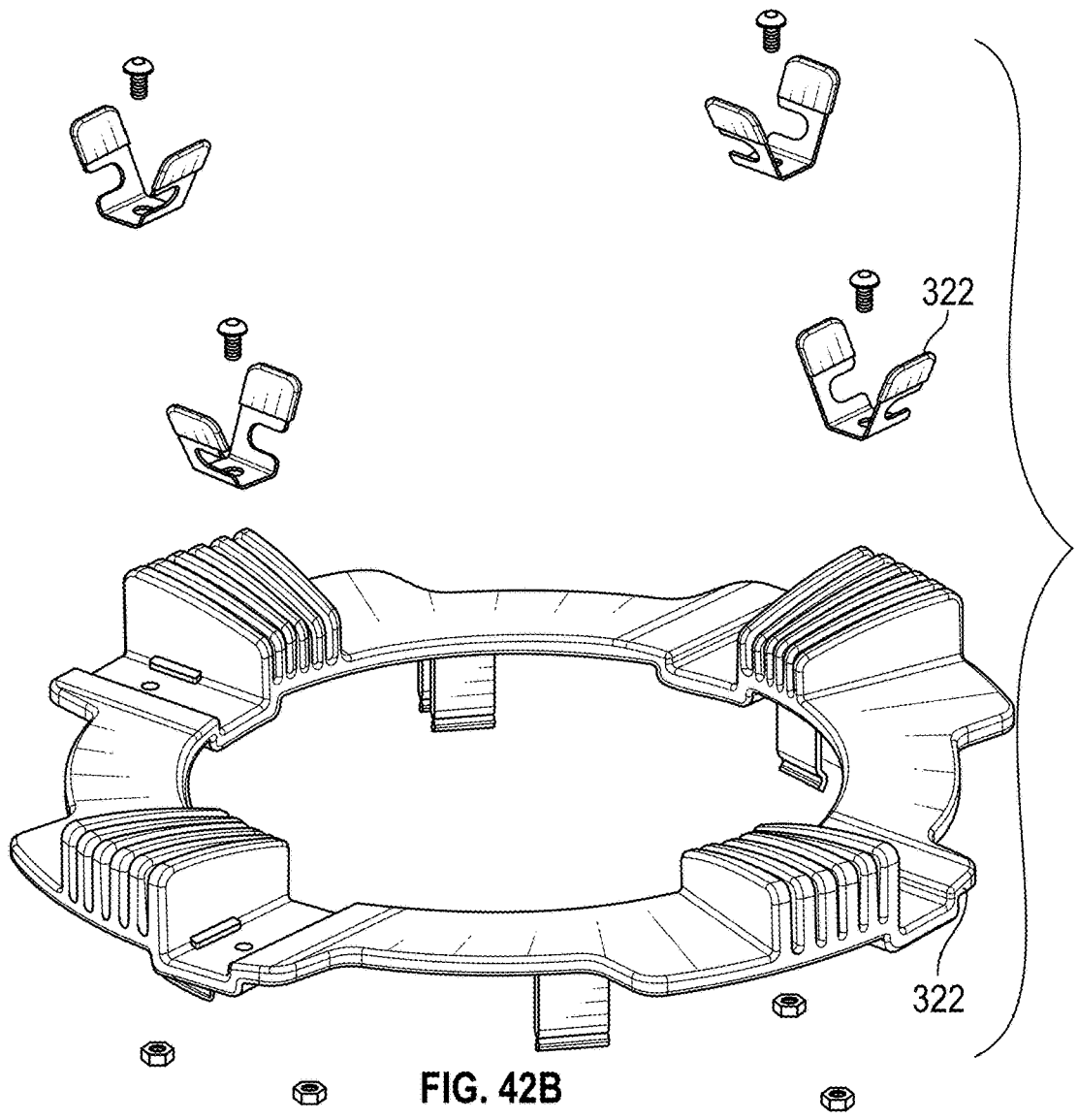

FIGS. 42A and B show assembled and exploded views of the platform 322. As illustrated, platform is ring shaped and defines an opening therethrough. Retractor rod clips 322 are made from a spring material, such as steel or molded plastic. The rod clips can be attached to platform 320 with fasteners such as screws, and define an opening through a side of each fin of each clip to receive a handle or rod of a respective retractor assembly 310. Platform also defines four sets of fins that cooperate to define five channels each to receive a corresponding set of cutter tethers 343 therethrough. Platform defines a plurality (in this example, 6) molded clips that extend downwardly therefrom that are configured to grab the rolling ring 330 with the inner bag 340 wrapped around it.

Figure 43A:
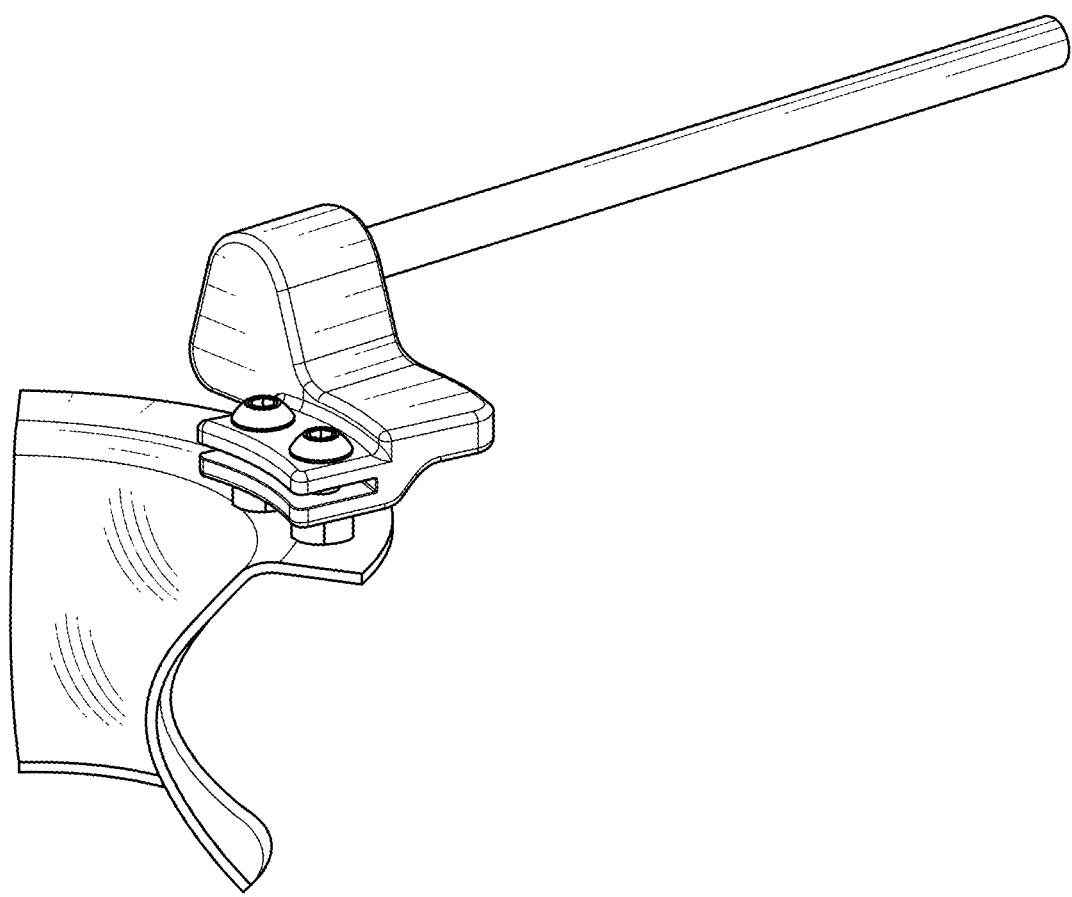
Figure 44A:
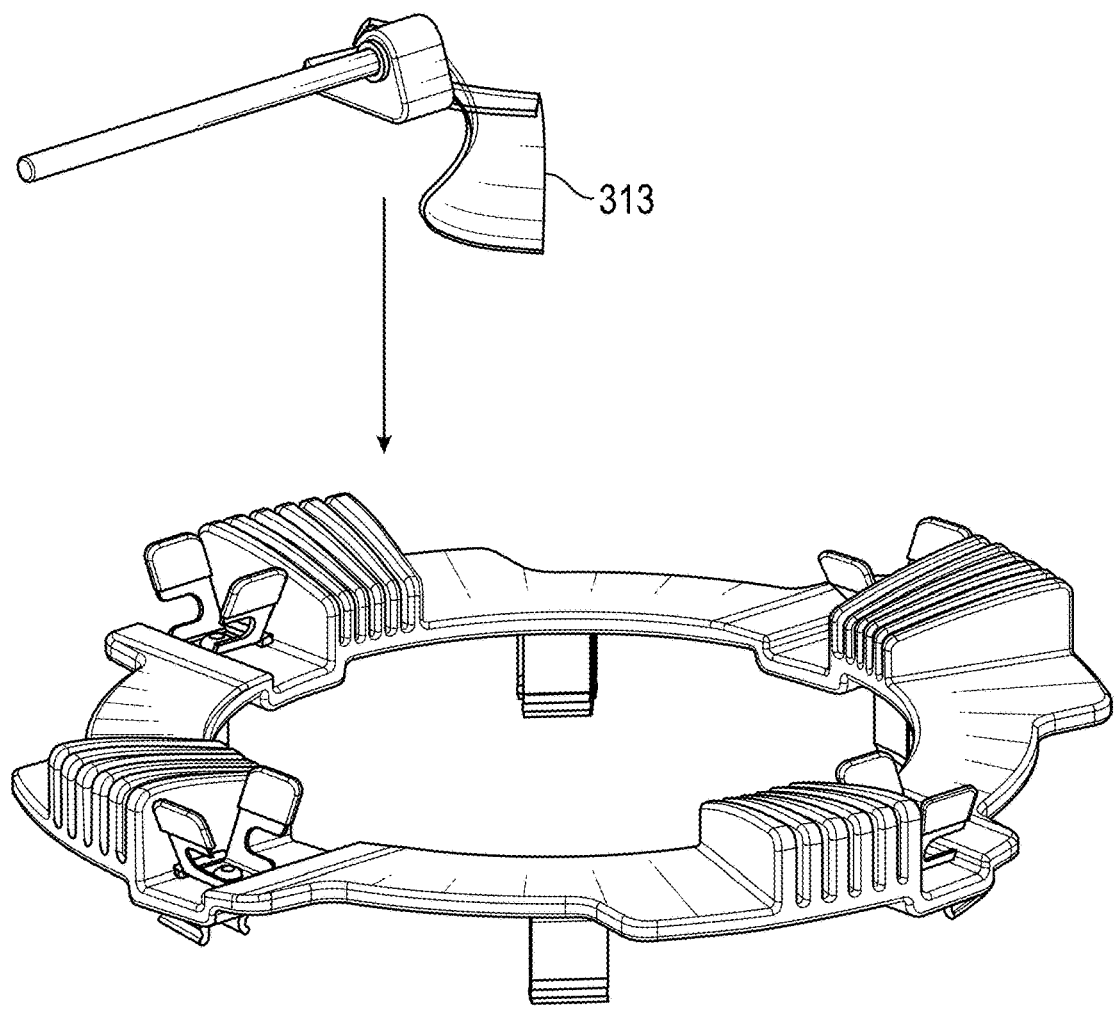
Figure 44B:
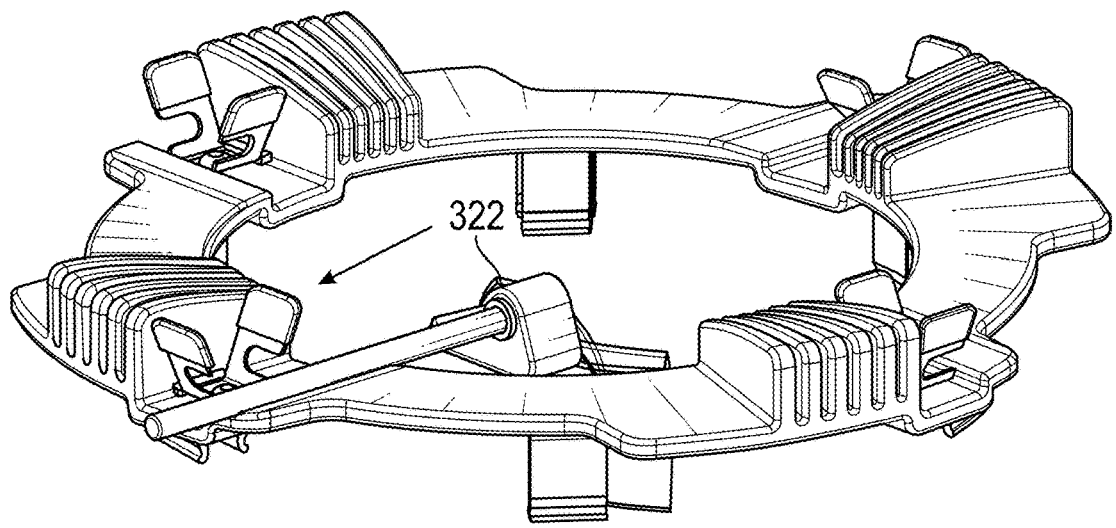
Figure 44C:
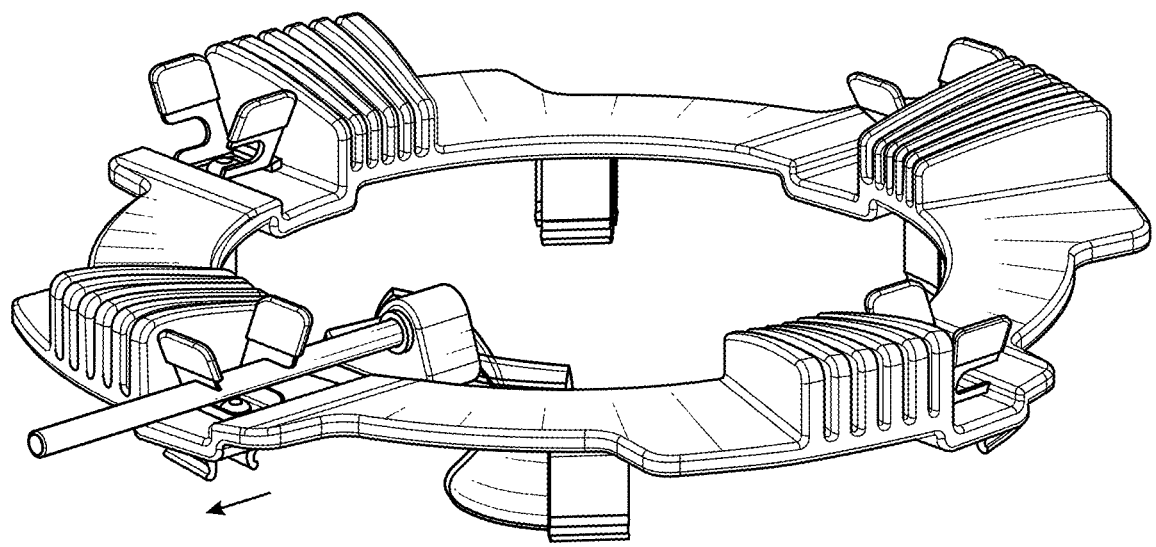
Figure 44D:
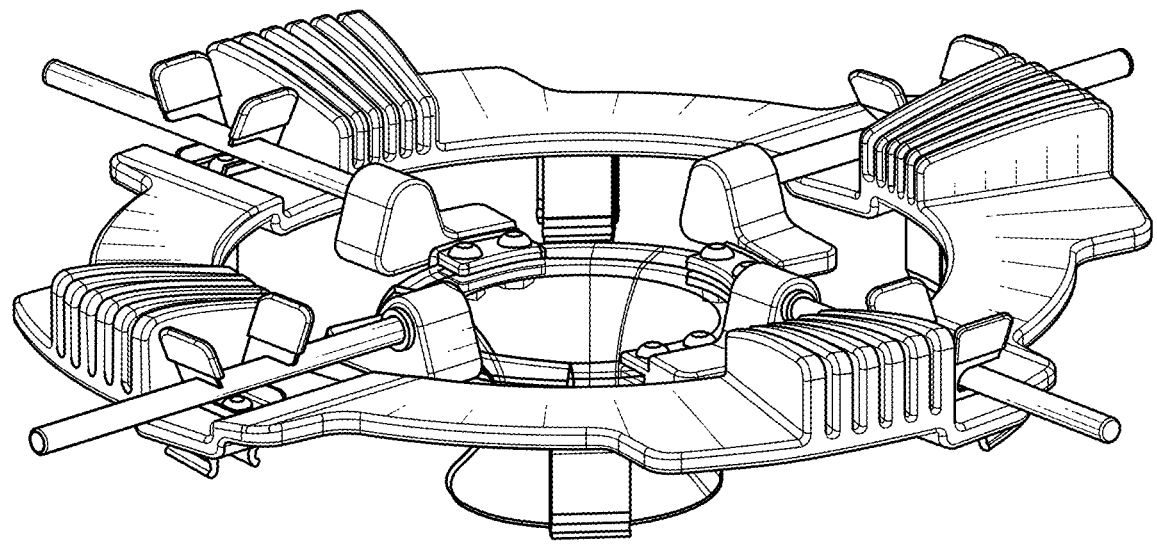

FIGS. 43A-43D illustrate aspects of retractor assemblies 310, which are received within openings defined through the wing portions of clips 322. The retractor assembly includes a rod shaped handle 311 having a free end and a second end. The second end is threadably received into an adapter 312. The adapter 312 couples the rod handle 311 to a retractor blade 313. In the illustrated example, the retractor blade 313 includes a flange defining openings therethrough that receive fasteners to hold the blade to the adapter. The blade is preferably made from an atraumatic polymeric molded material, and adjacent blades are preferably wide enough to overlap to cooperate to form a wound protector. FIG. 43A shows the retractor assembly, FIG. 43B shows an exploded view of the assembly, FIG. 43C shows a front and side view of the blade 313, and FIG. 43D shows a top view of the blade 313. It will be appreciated with respect to FIG. 43D that the angular extent in top view of the blade is over 90 degrees (in this example, 110 degrees) to permit adjacent blades 313 to overlap. It will be appreciated that the platform 320 can be configured to hold fewer or more than 4 blades, if desired. As such, if three blades were used that were evenly spaced, they can each have an angular extent, for example, of 140-150 degrees, and if five or more blades are used, they can have an angular extent less than 90 degrees, as desired.

FIGS. 44A-44D illustrate the manner in which retractor assemblies 310 are mounted on platform 320. The blade 313 is first pushed into the incision, and then the rod 311 is received within clip 322. The arms of the clip are squeezed together, permitting the rod to be slid radially outward. Afterwards, the clip is released and the rod 311 is held in place. The procedure can then be repeated for the other three retractor assemblies 310. This is performed after the platform has been attached to the rolling ring 330 and inner bag 340, and after the outer bag 360 is partially withdrawn and folded over.

Figure 45A:
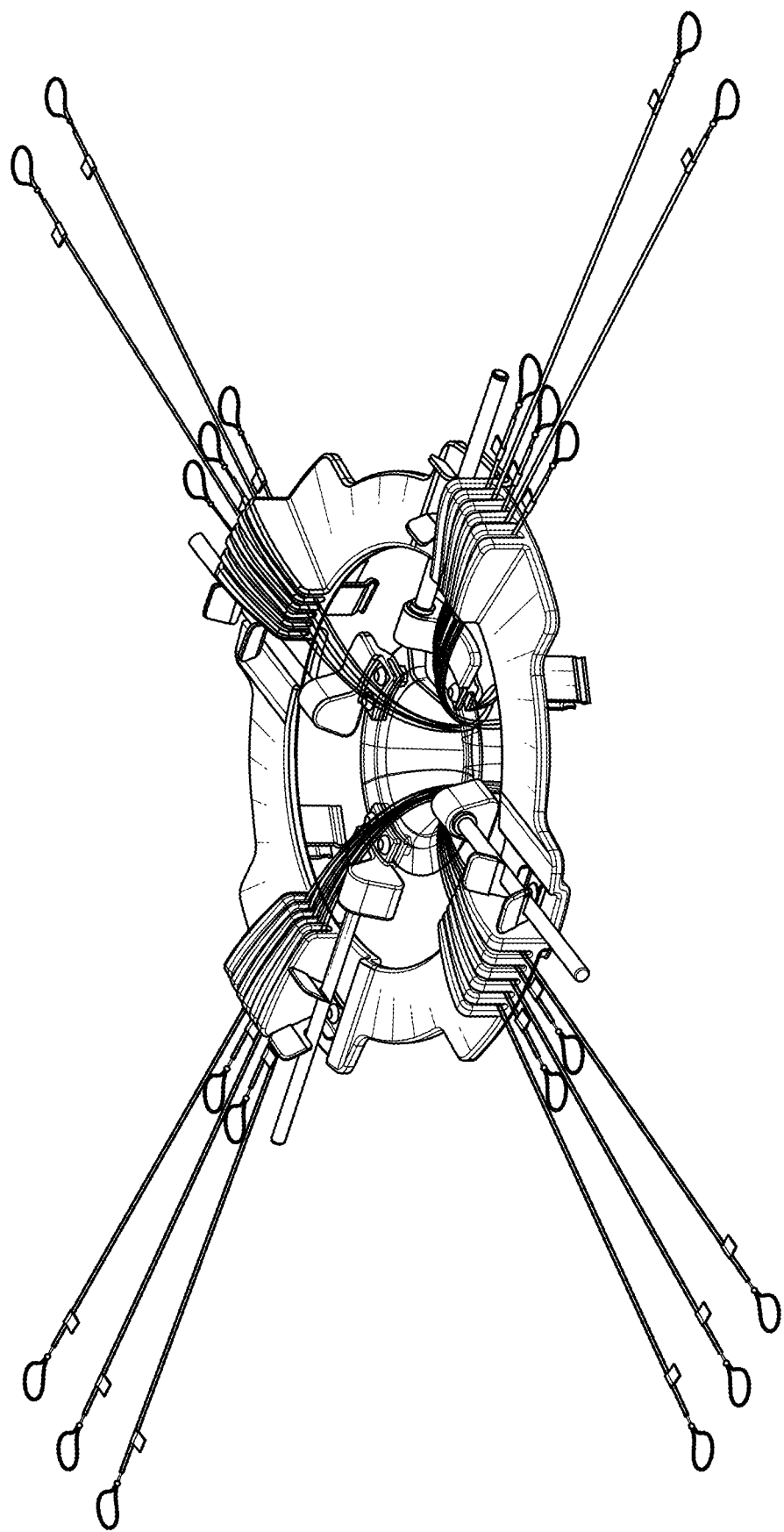
Figure 45B:
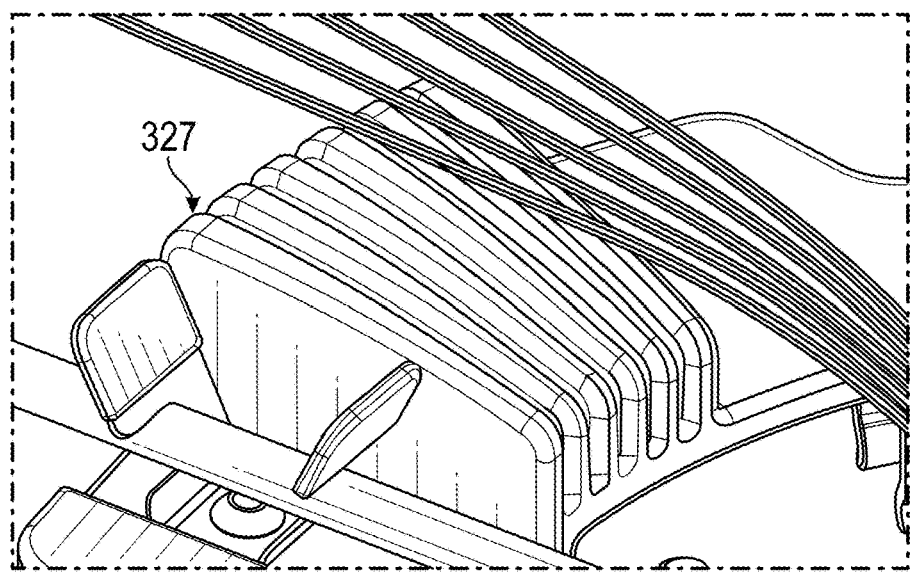
Figure 46:
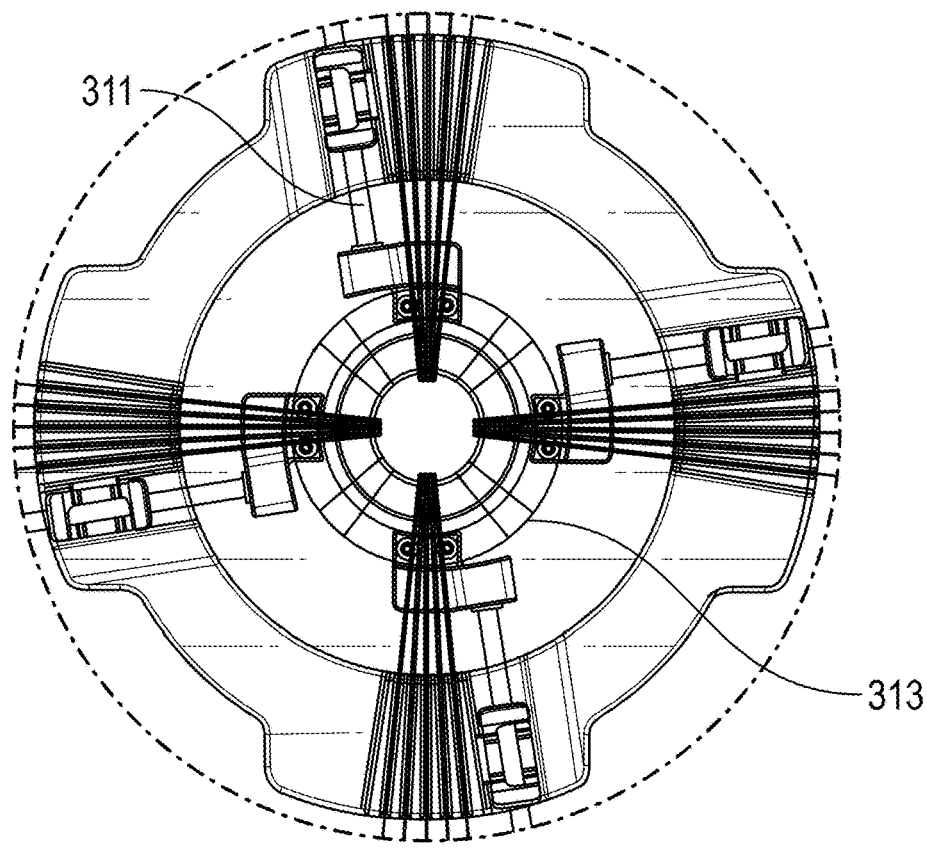

FIG. 45 A illustrates the cutters 343 after they have been withdrawn from the bag 340 to prepare to cut tissue. Each tether 343a is placed in a respective slot defined between adjacent fins 327 of the platform 320. FIG. 45 B is a close up view showing the fins 327 and the cutter tethers 343. At this point in the procedure, the blocks 345 have been removed from the bag 340 to permit the tethers 343a to be placed. The tubing covering the tethers discussed above prevent snagging on the support 320 and retractor assemblies 310. As can be seen in FIG. 46, the linear direction of each retractor handle rod 311 is offset but parallel to the diameter of the platform to prevent the retractor from interfering with the passage of the tethers 343a. As such, the retractor blade 313 is laterally offset from the rod 311 by way of adapter 312. But, the retractor blades 313 are aligned with the cutting directions so that the tethers 313 are circumferentially displaced from the joints between the retractor blades.

Figure 47A:
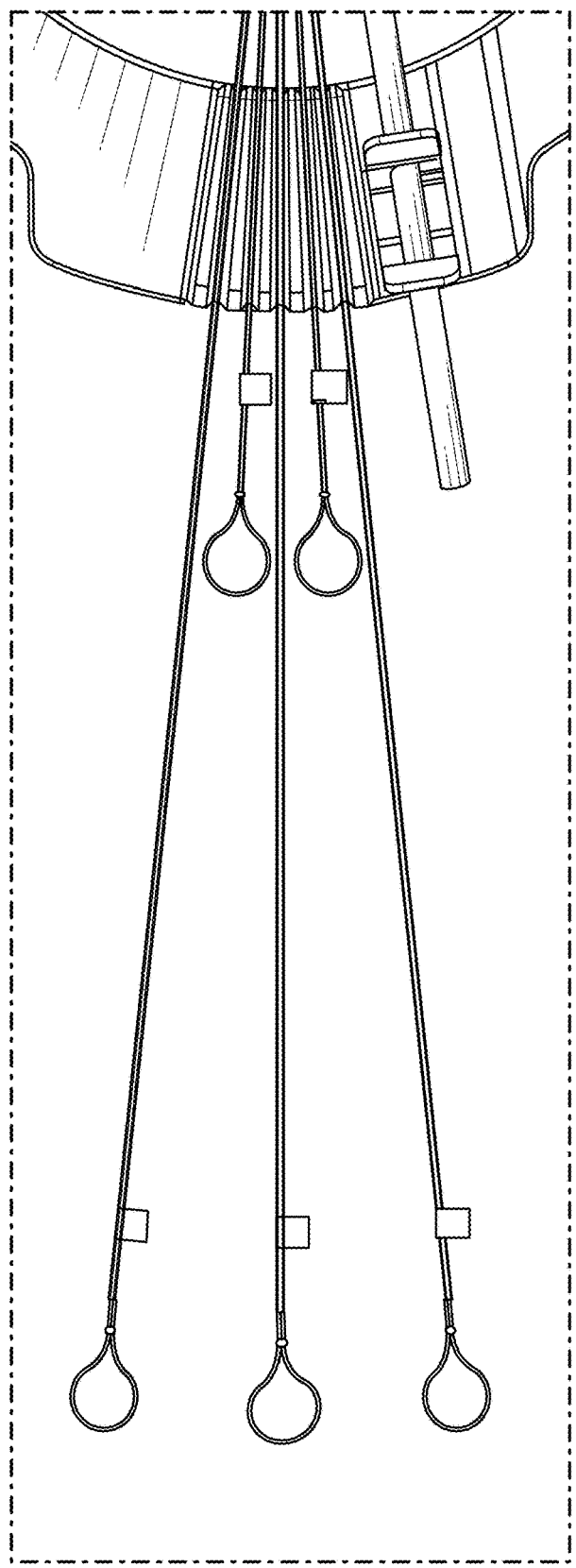
Figure 47B:
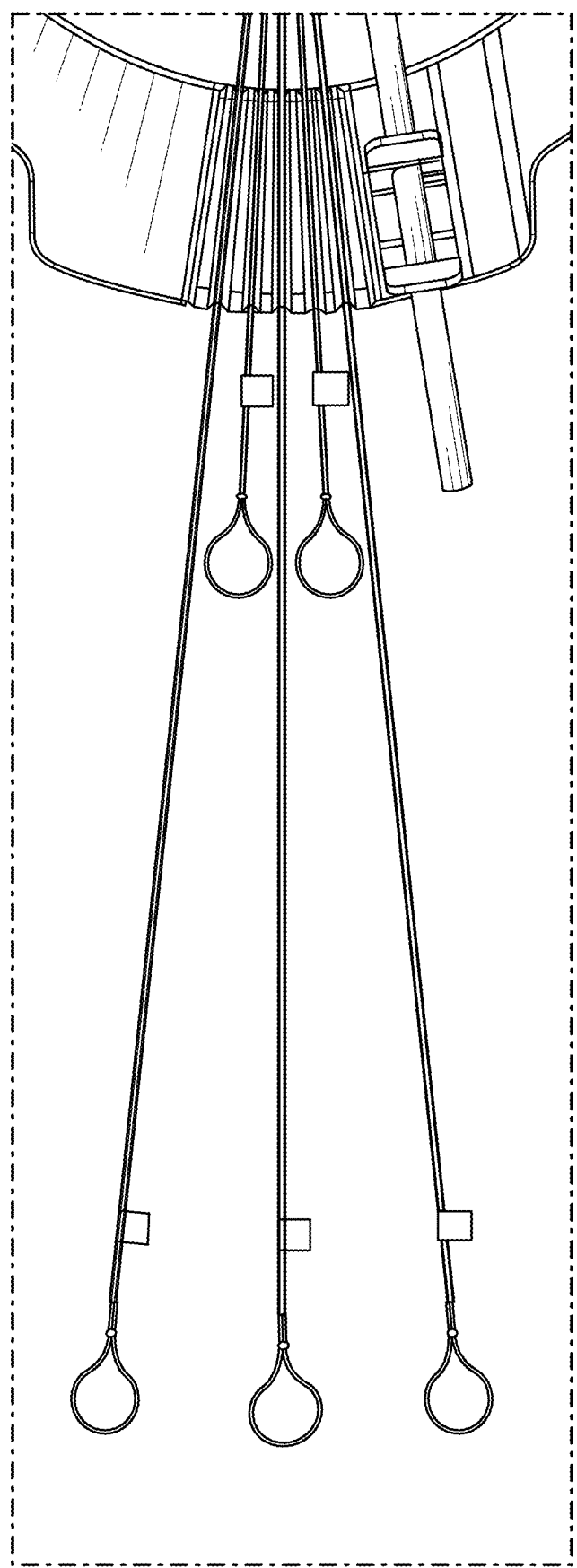
Figure 47C:
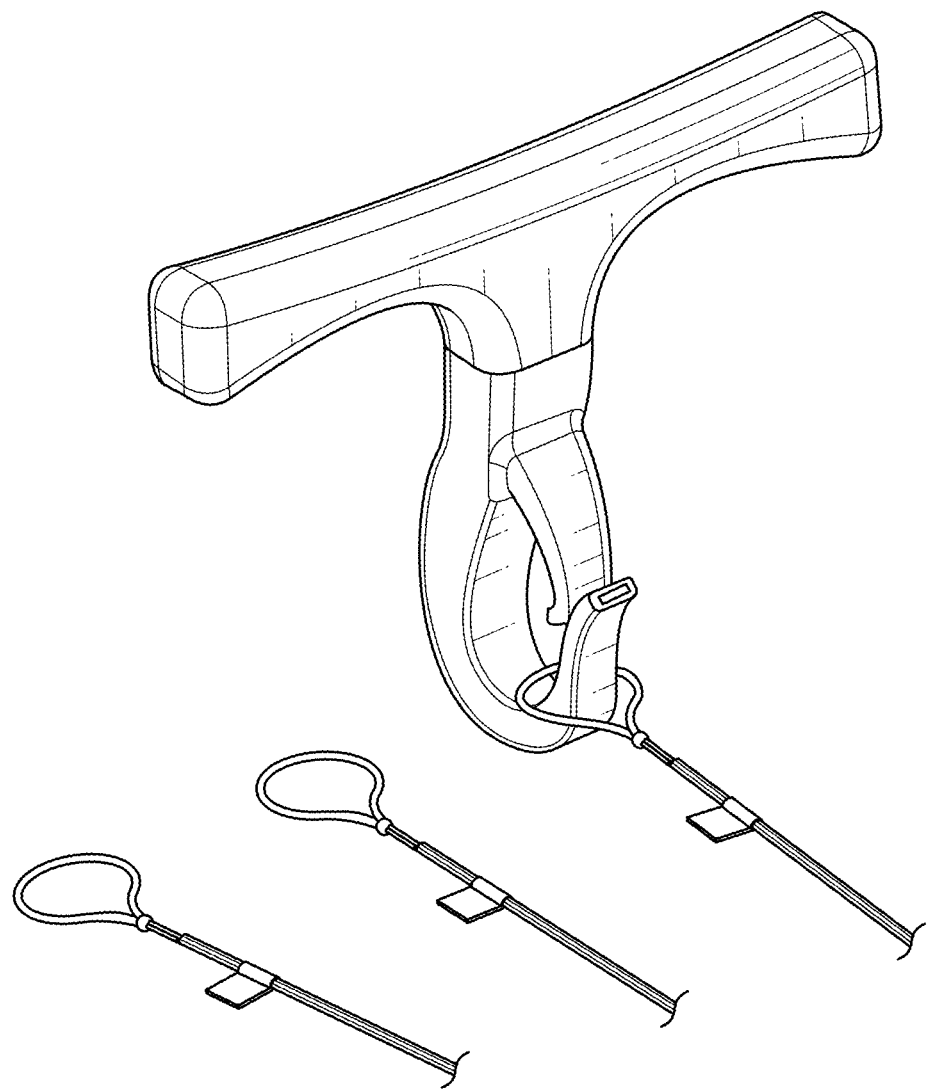

With respect to FIGS. 47A-47C, an illustrative cutting sequence is presented. The tethers can be numerically coded with indicia as illustrated to indicate the order in which the tethers and cutters are used. For example, in FIG. 47A, the first cutting sequence is "outside" to "inside" following labels 1-5 in order. Along the second cutting direction, as shown in FIG. 47B, the sequence is also outside to inside and numerically coded. FIG. 47C illustrates the coupling of the tethers 343a to the cutting handles.

The following is an example method of use of system 300. An incision (e.g., 2.5 centimeters (cm) long) is created in a patient's skin with a knife (e.g., scalpel). A cannula assembly 500, for example, one having a 2.8 cm diameter, is inserted through the incision using a metal and/or plastic trocar (e.g., a taper point or cutting/trocar point). The inner diameter of the cannula should be at least the length of the incision (e.g., 2.5 cm). The trocar is then removed, but the cannula is left in place. In so doing, the first stroke begins by pulling on the "shorter" end of the cutter 343 as described herein above.

A bag, such as bag 340 contains a plurality of molded, flexible tracks/guides for a plurality of cutters 343. Each cutter 343 preferably has a color-coded and/or numbered handle coupled to each end of the cutters. For example, if there are four cutting elements then there are eight color-coded and numbered handles.

The upper portions of the cutter strands are held in place against the sides of the bag (e.g., with plastic tabs) so that they do not become tangled when the bag is rolled or compressed. The handles can be staggered in height so as to facilitate passing the bag through the cannula.

The bag is inserted (pushed) into the patient's body (e.g., the patient's abdomen) through the cannula using an inserter with the bag rolled up (like an umbrella) inside the inserter. The cannula can include a seal that can be used as visual port, for example, for a camera. A camera can facilitate inserting a tissue specimen into the bag. Once the bag is inserted into the patient, the bag lies free. The tissue specimen is then inserted into the bag.

After inserting the tissue specimen in the bag, the neck of the bag is grasped (e.g., with a grasper) and pulled up through the incision. The cannula is then removed. Small tags can be fastened to the edge of the bag to facilitate this process. The ring handles and cutting elements and/or strands are pulled away/detached from the sides of the bag. The bag is attached to bag rolling ring 330 via hooks 332 and rolled taut. Rolling the bag with bag rolling ring 330 may require four hands. To facilitate rolling the bag can be brought up taut against the underside of the incision (e.g., against the abdominal wall). Once the bag is rolled taut such that the tissue specimen is held against the underside of the incision, the cutting elements and/or strands are brought up through the annulus of bag rolling ring 330. Platform 320 is coupled to (e.g., snapped onto) bag rolling ring 330 with the end of bag 340 rolled around it, holding the bag 340 in place. The cutters 343 can be removably attached to the platform 320 as illustrated herein.

The cutters 343 can be individually removed from the inner surface of the bag 340 and any retainers, one at a time, and pulled back and forth in a sawing motion. The cutters quickly reduce the tissue specimen to smaller, manageable sized pieces. When one of the cutters and/or strands cuts all the way through the tissue specimen, that cutting element or strand is removed. The cutters 343 are utilized and removed sequentially according the numbers assigned to each of the handles. After all of the cutting elements and/or strands have cut through the tissue specimen and have been removed through the opening of disc platform, the platform 320 is separated and/or removed from the bag, and the inner bag 340 and outer bag 360 are removed from the patient.

One or more components of embodiments of the present disclosure can be single-use and/or disposable.

It is contemplated that any of the rings disclosed herein may be made of silicone, polymer, metal, or any other suitable material. Where a ring has parts with different flexibilities/rigidities, the more flexible part may be made of a more flexible material (e.g., silicone), and the more rigid part may be made of a more rigid material (e.g., plastic or metal).

It will be apparent to those skilled in the art that various modifications and variations can be made in the disclosed devices and methods without departing from the scope of the disclosure. Other aspects of the disclosure will be apparent to those skilled in the art from consideration of the specification and practice of the features disclosed herein. It is intended that the specification and examples be considered as illustrative only.

What is claimed is:

1. A tissue extraction device, comprising:
   a bag made from a layer of material having an open proximal end and a closed distal end, the bag defining an interior bounded by an inner surface; and
   at least one cutter extending through the interior of the bag along an inner surface of the bag, wherein the at least one cutter includes a first strand and a second strand coupled to at least one blade assembly, wherein the at least one blade assembly includes a plurality of links that are pivotally connected to one another to form a cutting chain, a first link in the plurality of links defines a cutting edge along a first side of the first link and a dulled edge on a second, opposing side of the first link, and a second link in the plurality of links that is pivotally coupled directly to the first link includes a dulled edge along a first side of the second link corresponding to the first side of the first link, and a sharpened edge along a second side of the second link corresponding to the second side of the first link to permit opposing edges of the cutting chain to cut tissue as the at least one cutter is drawn across tissue.

2. The tissue extraction device of claim 1, wherein the at least one blade is removably attached to the inner surface of the bag at a location displaced from the closed distal end of the bag.

3. The tissue extraction device of claim 1, wherein the at least one cutter includes a plurality of individual cutters arranged parallel to each other, wherein the at least one blade of adjacent cutters are located on opposing sides of the inner surface of the bag.

4. The tissue extraction device of claim 1, further comprising a rolling ring, wherein a proximal portion of the bag is configured to be rolled around the rolling ring.

5. The tissue extraction device of claim 4, wherein the rolling ring includes a ring body defining at least one protrusion to engage a portion of the bag.

6. The tissue extraction device of claim 5, wherein a proximal portion of the bag defines one or more holes to receive the at least one protrusion of the retractor ring after at least one detachable section has been detached from the bag.

7. The tissue extraction device of claim 4, further comprising a frame including at least one fastener to couple to and retain the rolling ring after a proximal portion of the bag has been rolled about the rolling ring.

8. The tissue extraction device of claim 1, wherein the first strand and second strand of the at least one cutter are about the same length, and further wherein the first strand extends from the open proximal end of the bag further than the second strand extends from the open proximal end of the bag.

9. The tissue extraction device of claim 3, wherein the plurality of cutters traverse a path along the inner surface of the bag parallel to one another along the closed distal end of the bag and that converge as the plurality of cutters approach the open proximal end of the bag.

10. The tissue extraction device of claim 9, wherein the plurality of cutters are received by a retainer coupled to the inner surface of the bag after the paths of the cutters have converged.

11. The tissue extraction device of claim 7, wherein the frame includes at least one retractor arm of a retractor, wherein the at least retractor arm is aligned with a direction that does not pass through a geometric center of the frame to permit the at least one cutter to pass over the frame along a direction parallel to a line that passes through the geometric center of the frame.

12. The tissue extraction device of claim 11, wherein the at least one retractor arm includes a plurality of retractor arms, each of the plurality of retractor arms including a retractor blade disposed at a radially inner end thereof, wherein edges of adjacent retractor blades disposed on the retractors overlap one another in an open central region of the frame to cooperatively form an annulus proximate an incision in a patient.

13. The tissue extraction device of claim 1, wherein the at least one blade is held in place against the inner wall of the bag within a blade holder subassembly.

14. The tissue extraction device of claim 1, wherein the first strand and the second strand are surrounded by a tubular member to facilitate sliding of the at least one cutter along the inner surface of the bag.

* * * * *